US009938526B2

(12) United States Patent
Sanchez-Ramos et al.

(10) Patent No.: US 9,938,526 B2
(45) Date of Patent: Apr. 10, 2018

(54) MANGANESE ION COATED NANOPARTICLES FOR DELIVERY OF COMPOSITIONS INTO THE CENTRAL NERVOUS SYSTEM BY NASAL INSUFFLATION

(71) Applicants: Juan Sanchez-Ramos, Plant City, FL (US); Vasyl Sava, Wesley Chapel, FL (US); Shijie Song, Tampa, FL (US); Shyam S. Mohapatra, Lutz, FL (US); Subhra Mohapatra, Lutz, FL (US)

(72) Inventors: Juan Sanchez-Ramos, Plant City, FL (US); Vasyl Sava, Wesley Chapel, FL (US); Shijie Song, Tampa, FL (US); Shyam S. Mohapatra, Lutz, FL (US); Subhra Mohapatra, Lutz, FL (US)

(73) Assignees: University of South Florida, Tampa, FL (US); The United States of America as Represented by the Department of Veterans Affairs Office of General Counsel—PSG IV (024), Washington, DC (US)

( * ) Notice: Subject to any disclaimer, the term of this patent is extended or adjusted under 35 U.S.C. 154(b) by 0 days.

(21) Appl. No.: 15/162,872

(22) Filed: May 24, 2016

(65) Prior Publication Data
US 2016/0312222 A1 Oct. 27, 2016

Related U.S. Application Data

(62) Division of application No. 14/343,534, filed as application No. PCT/US2012/055306 on Sep. 14, 2012, now Pat. No. 9,375,400.

(60) Provisional application No. 61/534,417, filed on Sep. 14, 2011.

(51) Int. Cl.
| | |
|---|---|
| *C12N 15/113* | (2010.01) |
| *A61K 31/713* | (2006.01) |
| *A61K 9/00* | (2006.01) |
| *A61K 9/107* | (2006.01) |
| *A61K 9/16* | (2006.01) |
| *A61K 9/50* | (2006.01) |
| *A61K 49/18* | (2006.01) |
| *C12N 15/88* | (2006.01) |
| *C12N 15/89* | (2006.01) |
| *A61K 9/51* | (2006.01) |
| *A61K 31/7088* | (2006.01) |
| *A61K 47/54* | (2017.01) |
| *A61K 47/69* | (2017.01) |
| *A61K 48/00* | (2006.01) |

(52) U.S. Cl.
CPC .......... *C12N 15/113* (2013.01); *A61K 9/0043* (2013.01); *A61K 9/1075* (2013.01); *A61K 9/1611* (2013.01); *A61K 9/1652* (2013.01); *A61K 9/1658* (2013.01); *A61K 9/50* (2013.01); *A61K 9/501* (2013.01); *A61K 9/5115* (2013.01); *A61K 31/7088* (2013.01); *A61K 31/713* (2013.01); *A61K 47/541* (2017.08); *A61K 47/547* (2017.08); *A61K 47/6939* (2017.08); *A61K 49/1881* (2013.01); *C12N 15/88* (2013.01); *C12N 15/895* (2013.01); *A61K 48/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 7,871,990 B1 | 1/2011 | Sung |
| 2005/0142072 A1 | 6/2005 | Birch |
| 2009/0232899 A1 | 9/2009 | David |
| 2014/0170077 A1 | 6/2014 | Sung et al. |

OTHER PUBLICATIONS

Mistry, A. et al. "Nanoparticles for direct nose-to-brain delivery of drugs" International Journal of Pharmaceutics, 2009, vol. 379, pp. 146-157.
Bae, K.H. et al. "Surface functionalized hollow manganese oxide nanoparticles for cancer targeted siRNA delivery and magnetic resonance imaging" Biomaterials, Oct. 9, 2010 (Epub), vol. 32, pp. 176-184.
Agyare, E.K. et al. "Development of a smart nano-vehicle to target cerebrovascular amyloid deposits and brain parenchymal plaques observed in Alzheimer's disease and cerebral amyloid angiopathy" Pharmaceutical Research, 2008, vol. 25, No. 11, pp. 2674-2684.
International Search Report and Written Opinion, dated Feb. 25, 2013.
Henriksson et al., (1999) Transport of Manganese via the Olfactory Pathway in Rats: Dosage Dependency of the Uptake and Subcellular Distribution of the Metal in the Olfactory Epithelium and the Brain. Toxicology and Applied Pharmacology. vol. 156, Issue 2, Apr. 15, 1999, pp. 119-128.

(Continued)

*Primary Examiner* — Robert M Kelly
(74) *Attorney, Agent, or Firm* — Thomas | Horstemeyer, LLP

(57) ABSTRACT

The compositions and methods of the disclosure particularly target the divalent metal transporter expressed on olfactory nerve terminals to transport divalent cation-coated or cation-containing nanoparticles to all regions of brain. It has been found that such divalent cation-containing nanoparticles, including those nanoparticles comprising manganese have affinity for the metal transport receptor proteins. Although this receptor has particular affinity for manganese, it is contemplated that other divalent ions, including magnesium, calcium, and the like may also be bound to such receptors leading to transport of the nanoparticles into the intracellular cytoplasm. Nanoparticles have been developed, therefore, as vehicles for parenteral delivery of genes, proteins and drugs. The present disclosure encompasses embodiments of nanoparticle-based compositions and methods for the use thereof for the delivery of genes, oligonucleotides, including but not limited to small interfering RNA, and other small molecule drugs, into the brain by nasal insufflation.

5 Claims, 15 Drawing Sheets

(56) References Cited

OTHER PUBLICATIONS

Kim et al., (2007) Chemical modification of chitosan as a gene carrier in vitro and in vivo. Progress in Polymer Science. vol. 32, Issue 7, Jul. 2007, pp. 726-753.
Rolland A. (2005) Gene medicines: The end of the beginning? Advanced Drug Delivery Reviews vol. 57, Issue 5, Apr. 5, 2005, pp. 669-673.
Shu & Zhu (2002) The influence of multivalent phosphate structure on the properties of ionically cross-linked chitosan films for controlled drug release. European Journal of Pharmaceutics and Biopharmaceutics vol. 54, Issue 2, Sep. 2002, pp. 235-243.
Lee et al., (2005) The use of chitosan as a condensing agent to enhance emulsion-mediated gene transfer. Biomaterials 26: 2147-2156.
Rao & Sharma (1997) Use of chitosan as a biomaterial: Studies on its safety and hemostatic potential. Biomed. Mater. Res. 34: 21-28.
Aspden et al., Chitosan as a nasal delivery system: the effect of chitosan solutions on in vitro and in vivo mucociliary transport rates in human turbinates and volunteers. J. Pharm. Sci. 86 (1997) 509-513.
Na et al., (2007) Development of a T1 contrast agent for magnetic resonance imaging using MnO nanoparticles. Angew. Chem. Int Ed 46: 5397-540.
Wang et al., (2011) Recent advances of chitosan nanoparticles as drug carriers. Int. J. Nanomed. 6: 765-774.
Huang et al., (2005) Transfection efficiency of chitosan vectors: effect of polymer molecular weight and degree of deacetylation. J. Control. Release 106: 391-406.
Sato et al., (2001) In vitro gene delivery mediated by chitosan. effect of pH, serum, and molecular mass of chitosan on the transfection efficiency. Biomaterials 22: 2075-2080.
MacLaughlin et al., (1998) Chitosan and depolymerized chitosan oligomers as condensing carriers for in vivo plasmid delivery. J. Control. Release 56: 259-272.
Nafee et al., (2007) Chitosan-coated PLGA nanoparticles for DNA/RNA delivery: effect of the formulation parameters on complexation and transfection of antisense ligonucleotides. Nanomedicine: Nanotechnol. Biol. Med. 3: 173-183.
Sunil et al., (2004) Recent advances on chitosan-based micro- and nanoparticles in drug delivery. J. Controlled Release 100: 5-28.
Bernkop-Schnurch et al., (2003) Thiolated polymers—thiomers: synthesis and in vitro evaluation of chitosan-2-iminothiolane conjugates. Int. J. Pharm. 260: 229-237.
Roldo et al., (2004) Mucoadhesive thiolated chitosans as platforms for oral controlled drug delivery: synthesis and in vitro evaluation. Eur. J. Pharm. Biopharm. 57: 115-121.
Langoth et al., (2006) Thiolated chitosans: design and in vivo evaluation of a mucoadhesive buccal peptide drug delivery system. Pharm. Res. 23: 573-579.
Kas H.S. (1997) Chitosan: properties, preparations and application to microparticulate systems. J. Microencapsul. 14: 689-711.
Ramaswamy, et al. (2012) Neurobiology of Disease 48: 243-54.
Bowman and Leong (2006) "Chitosan nanoparticles for oral drug and gene delivery", International Journal of Nanomedicine, 1 (2): 117-28.
Thompson, et al. (201 0) "Manganese Uptake and Distribution in the Brain after Methyl Bromide-Induced Lesions in the Olfactory Epithelia", Toxicology Science, 120(1 ): 163-72.

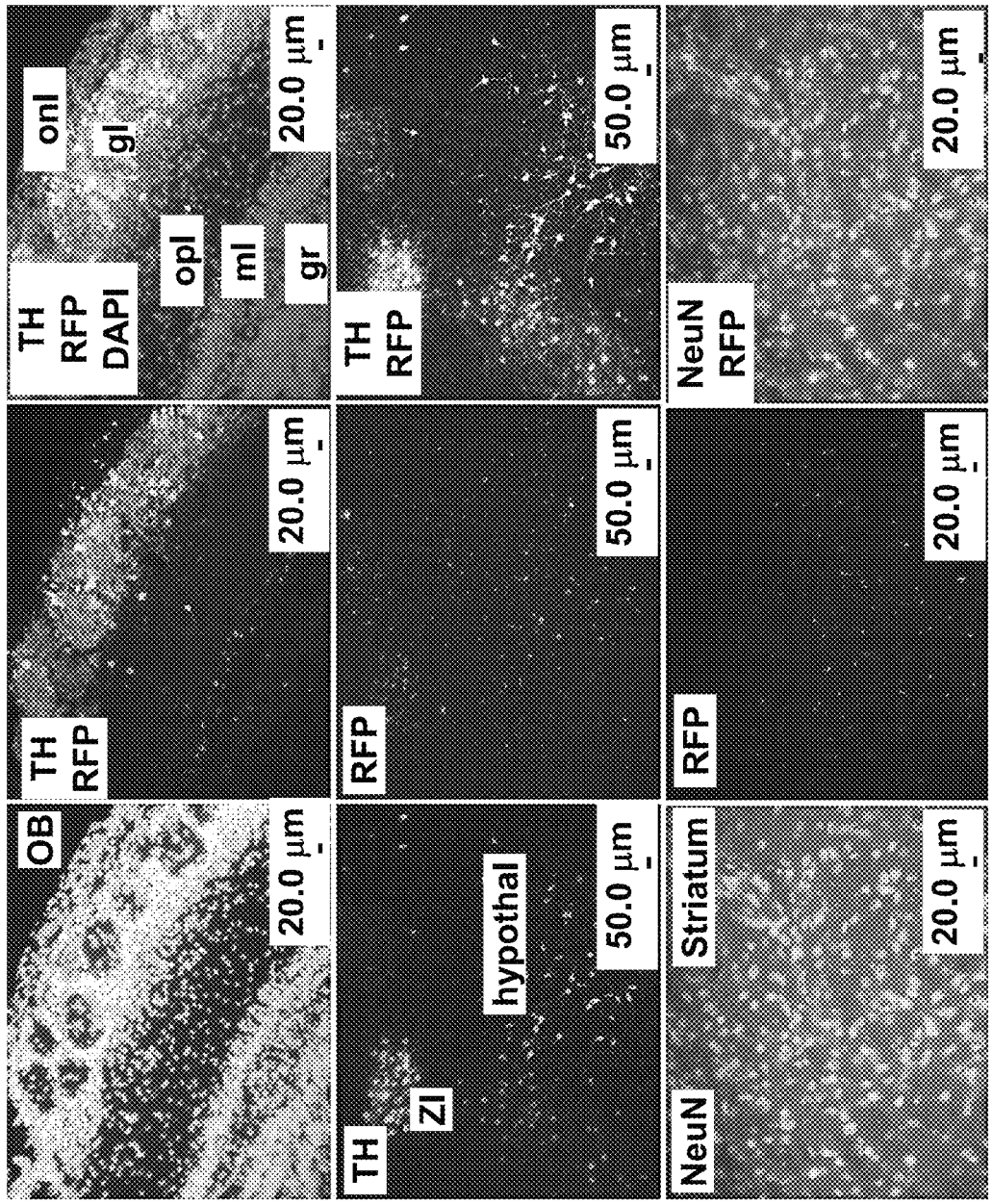

MANGANESE ION COATED NANOPARTICLES FOR DELIVERY OF COMPOSITIONS INTO THE CENTRAL NERVOUS SYSTEM BY NASAL INSUFFLATION

CROSS-REFERENCE TO RELATED APPLICATIONS

This application is a Divisional of U.S. patent application entitled "DIVALENT-METAL COATED NANOPARTICLES FOR DELIVERY OF COMPOSITIONS INTO THE CENTRAL NERVOUS SYSTEM BY NASAL INSUFFLATION" filed on May 19, 2014 and assigned serial number 14/343,534, which claimed the benefit of PCT/US2012/055306 filed Sep. 14, 2012, which claimed the benefit of U.S. provisional patent application 61/534,417, filed Sep. 14, 2011, the contents of which are herein incorporated by reference in their entireties.

TECHNICAL FIELD

The present disclosure is generally related to nanoparticles incorporating a divalent metal and which are suitable for the delivery of an agent to the brain via the olfactory cells of the nasal passage. The present disclosure is further related to methods of using said delivery vehicle to deliver an agent to the brain of a subject.

BACKGROUND

Manganese is transported into brain by olfactory neurons. Manganese and manganese oxide particles are known to accumulate in brain tissue in welders and in manganese miners resulting in neurotoxic manifestations. Homeostatic mechanisms keep blood manganese levels tightly controlled, but over-exposure can overload the excretion process resulting in toxic accumulation of the metal in the globus pallidus and other brain regions. Welders and miners with over-exposure have had MRI images taken that reveal increased signal in the globus pallidus (structure of the basal ganglia) under T-1 weighted conditions. However, clearance of manganese and reversal of the image to normal occurs when subjects are taken out of the toxic environment, emphasizing powerful homeostatic mechanisms to keep manganese tissue levels within a narrow range.

Manganese, like gadolinium, is useful as a contrast agent. Infusion of manganese oxide into the venous system will permit visualization in the brain of leaky blood vessels associated with various disease processes such as stroke, inflammation, trauma.

The mechanism of transport of manganese into the brain via the olfactory system, when studied in rat, revealed that manganese transport was saturable when considering uptake into olfactory bulb (Henriksson et al., (1999) *Toxicol. App. Phamacol.* 156: 119-128). In addition, manganese was reported to move relatively freely from the olfactory bulb to olfactory cortex and other regions of brain. Thus, olfactory neurons provide a pathway with considerable capacity to transport manganese into the brain.

Nanoparticles can be designed to deliver genes of interest to specific targets such as tumors. Delivery of therapeutic genes into the central nervous system has mostly relied on stereotaxic neurosurgical injection into the brain of gene products (e.g. growth factors) or viral vectors that can include a gene of interest desired to be expressed in the brain. For chronic diseases like Huntington's disease that afflict the entire brain over extended periods, injection of a vector into multiple brain regions for a prolonged time make it unfeasible and unacceptable. Another problem with the current state of the art is the reliance on viral vectors (adeno-associated viruses or lentiviruses) to deliver a nucleic acid of interest. Applying these vectors to humans carries a degree of risk that is often unacceptable and can be obviated by using other vehicles for gene delivery such as nanoparticles designed to target specific tissues.

Gene delivery technology has grown very rapidly with applications designed to replace defective genes, substitute missing genes, or silence undesirable gene expression. However, naked genes are rapidly degraded by nucleases, showing poor cellular uptake, low target specificity, and inadequate transfection efficiency (Kim et al., (2007) *Prop. Polym. Sci.* 32: 726-753). Therefore, the development of efficient gene carriers is one of the prerequisites for the realization of gene therapy (Rolland A. (2005) *Adv. Drug Deliv. Rev.* 57: 669-673). Recently, chitosan-based carriers have become one of the major non-viral vectors that have received increasing interest as a reliable gene or siRNA delivery system. Chitosan has low toxicity, low immunogenicity, excellent biocompatibility (Shu & Zhu (2002) *Eur. J. Pharm. Biopharm.* 54: 235-243; Lee et al., (2005) *Biomaterials* 26: 2147-2156). Due to its positive charge, it can easily form polyelectrolyte complexes with negatively charged nucleotides by electrostatic interaction. However, the efficiency of chitosan to deliver gene therapy is significantly influenced by formulation.

Chitosan is obtained by deacetylation of chitin, which is the biodegradable polysaccharide consisting of repeating D-glucosamine and N-acetyl-D-glucosamine units, linked via (1-4) glycosidic bonds. Chitosan is almost non-toxic in animals (Rao & Sharma (1997) *Biomed. Mater. Res.* 34: 21-28) and humans (*Aspden et al., J. Pharm. Sci.* 86 (1997) 509-513), with an LD50 in rats of 16 g/kg (Chandy & Sharma (1990) *Biomater Artif Cells Artif Organs* 18: 1-24). Chitosan can be characterized by several physicochemical properties, including molecular weight, degree of deacetylation, viscosity, and crystallinity (Kas H. S. (1997) *J. Microencapsul.* 14: 689-711). The desirability of chitosan as a gene delivery carrier is based on its cationic property to allow binding of negatively charged siRNA via electrostatic interactions.

SUMMARY

One aspect of the present disclosure, therefore, encompasses embodiments of a method of delivering a therapeutic agent via an olfactory nerve to the central nervous system (CNS) of an animal or human subject, the method comprising administering to the nasal epithelium of the animal or human subject a pharmaceutically acceptable composition comprising a nanoparticle delivery vehicle, where the nanoparticle delivery vehicle can comprise a nanoparticle core, a therapeutic agent desired to be delivered to the brain of a recipient subject, and a divalent metal having binding affinity for a divalent metal transporter of an olfactory nerve terminal, where the divalent metal can be a metal ion, a metal oxide, a metal ion nanoparticle, a metal oxide nanoparticle, or any combination thereof, where the divalent metal can be selected from manganese, magnesium, zinc, copper, nickel, iron, lead, cadmium, and calcium, whereupon the divalent metal can selectively binds to a divalent metal transporter of an olfactory nerve cell, and the nanoparticle delivery vehicle be internalized by said cell, migrating at least to the olfactory bulb of the CNS of the recipient animal or human subject.

In some embodiments of this aspect of the disclosure, the divalent metal is manganese.

In some embodiments of this aspect of the disclosure, the divalent metal when in the central nervous system of an animal or human subject can be detectable by imaging.

In some embodiments of this aspect of the disclosure, the nanoparticle core can comprise chitosan, a derivative thereof, or a polymerized chitosan or a derivative thereof.

In embodiments of this aspect of the disclosure, the nanoparticle core comprises chitosan, a derivative thereof, or a polymerized chitosan or a derivative thereof, and wherein said chitosan, the derivative thereof, the polymerized chitosan, or the derivative thereof, can be cross-linked by a cross-linker.

In embodiments of this aspect of the disclosure, the cross-linker can have bound thereto a metal divalent ion having affinity for a divalent metal transporter of an olfactory nerve cell.

In embodiments of this aspect of the disclosure, the nanoparticle can further comprise a biocompatible layer on the surface thereof.

In embodiments of this aspect of the disclosure, the biocompatible layer can further comprise a moiety having affinity for the divalent metal.

In embodiments of this aspect of the disclosure, the moiety having affinity for the divalent metal ion can be poly(L-histidine) or a chelating agent.

In embodiments of this aspect of the disclosure, the therapeutic agent to be delivered to the central nervous system of an animal or human subject can be selected from a nucleic acid, a protein, a peptide, a therapeutic agent, or a combination thereof, where the nucleic acid can be a single strand DNA, a double strand DNA, or an RNA, and where said nucleic acid can be selected from the group consisting of: an oligonucleotide, a vector comprising a nucleotide sequence desired to be expressed in a recipient cell of the central nervous system of an animal or human subject, an isolated nucleic acid, and a recombinant nucleic acid.

In embodiments of this aspect of the disclosure, the nucleic acid can be an siRNA.

In embodiments of this aspect of the disclosure, the method can further comprise the step of detecting the nanoparticle delivery vehicle in the recipient animal or human subject, thereby forming an image of the distribution of the nanoparticle delivery vehicle in a tissue of the central nervous system of an animal or human subject.

Another aspect of the disclosure encompasses embodiments of a nanoparticle delivery vehicle, the vehicle comprising: a nanoparticle core comprising chitosan, a derivative thereof, or a polymerized chitosan or a derivative thereof; and a divalent metal having binding affinity for a divalent metal transporter of an olfactory nerve terminal.

In embodiments of this aspect of the disclosure, the divalent metal can be disposed on the surface of the nanoparticle core.

In embodiments of this aspect of the disclosure, the divalent metal can be embedded in the nanoparticle core.

In embodiments of this aspect of the disclosure, the divalent metal can be a metal, a metal ion, a metal oxide, a metal ion nanoparticle, a metal oxide nanoparticle, or any combination thereof.

In embodiments of this aspect of the disclosure, the divalent metal can be selected from the group consisting of manganese, magnesium, zinc, iron, copper, nickel, lead, cadmium, and calcium.

In embodiments of this aspect of the disclosure, the divalent metal can be manganese.

In embodiments of this aspect of the disclosure, the divalent metal can be detectable by imaging when in the central nervous system of an animal or human subject.

In embodiments of this aspect of the disclosure, the nanoparticle core can further comprise a therapeutic agent desired to be delivered to the central nervous system of the animal or human subject, wherein said agent is attached to, or embedded in, the nanoparticle core.

In embodiments of this aspect of the disclosure, the therapeutic agent can be attached to the nanoparticle core.

In embodiments of this aspect of the disclosure, the therapeutic agent can be embedded in the nanoparticle core.

In embodiments of this aspect of the disclosure, the chitosan, the derivative thereof, the polymerized chitosan, or the derivative thereof, can be cross-linked by a cross-linker selected from the group consisting of: L-(+)-Tartaric acid, ethylenediamine-N,N;,N;-triacetic acid, protoporphyrin IX, nitrilotriacetic acid, mercaptosuccinic acid, and ethylenediaminetetraacetic acid.

In embodiments of this aspect of the disclosure, the nanoparticle core can have a biocompatible layer disposed on the surface of said nanoparticle core and the divalent metal can be disposed on, or embedded in, the biocompatible layer, and wherein the divalent metal is available for binding to a cell surface receptor.

In embodiments of this aspect of the disclosure, the biocompatible layer can further comprise a moiety having affinity for the divalent metal.

In embodiments of this aspect of the disclosure, the moiety having affinity for the divalent metal ion can be poly(L-histidine) or a chelating agent.

In embodiments of this aspect of the disclosure, the therapeutic agent to be delivered to the central nervous system of an animal or human subject can be selected from a nucleic acid, a protein, a peptide, a therapeutic agent, or a combination thereof.

In embodiments of this aspect of the disclosure, the nucleic acid can be a single strand DNA, a double-strand DNA, a single strand RNA, or a double-strand DNA.

In embodiments of this aspect of the disclosure, the nucleic acid can be selected from the group consisting of: a polynucleotide, an oligonucleotide, an expression vector comprising a nucleotide sequence desired to be expressed in a recipient cell of the central nervous system of an animal or human subject, an isolated nucleic acid, or a recombinant nucleic acid.

In embodiments of this aspect of the disclosure, the nucleic acid can be an siRNA.

In embodiments of this aspect of the disclosure, the therapeutic agent to be delivered to the central nervous system of an animal or human subject can be selected from a nucleic acid, a protein, a peptide, a therapeutic agent, or a combination thereof, wherein the nucleic acid is a single strand DNA, a double strand DNA, or an RNA, and wherein said nucleic acid is selected from the group consisting of: an oligonucleotide, a vector comprising a nucleotide sequence desired to be expressed in a recipient cell of the central nervous system of an animal or human subject, an isolated nucleic acid, and a recombinant nucleic acid.

In embodiments of this aspect of the disclosure, the nucleic acid is an siRNA.

Yet another aspect of the disclosure encompasses embodiments of a pharmaceutical composition comprising a nanoparticle delivery vehicle according to claim 13 and a pharmaceutically acceptable carrier, wherein said pharmaceutical composition is formulated for administering the nanoparticle delivery vehicle to the nasal epithelium for binding of the delivery vehicle to a divalent metal transporter protein.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A-3D is a series of digital images illustrating the expression of red fluorescent protein (RFP) in olfactory bulbs, hypothalami and striata of mice treated with nasally-instilled Managanese-containg nanoparticles containing DNA encoding RFP. Mice were euthanized 24 hours after intranasal instillation of the nanoparticles.

FIG. 3A is an image of an olfactory bulb. Left panel: Structure of the olfactory bulb is visualized with DAPI staining, which stains all cell nuclei. Middle panel: Tyrosine hydroxylase (TH) immunostaining in green identifies dopaminergic neurons located in the glomerulosa layer.

Red identifies cells that express red fluorescent protein (RFP), indicating that the plasmid DNA encapsulated in the Managanese-containg nanoparticles is expressed. Right panel: Merged image of DAPI, TH and RFP.

FIG. 3B is an image of a hypothalamus and zona incerta (ZI). Left panel shows TH+ neurons located in hypothalamus and ZI. Middle panel demonstrates expression of RFP. Right panel is merged image of TH and RFP.

FIG. 3C illustrates the ventral striatum. Left panel: neurons immunostained with antibodies against neuron specific nuclear protein (NeuN); Middle panel: RFP expression; right panel: merged image of NeuN and RFP.

Figure 3D:
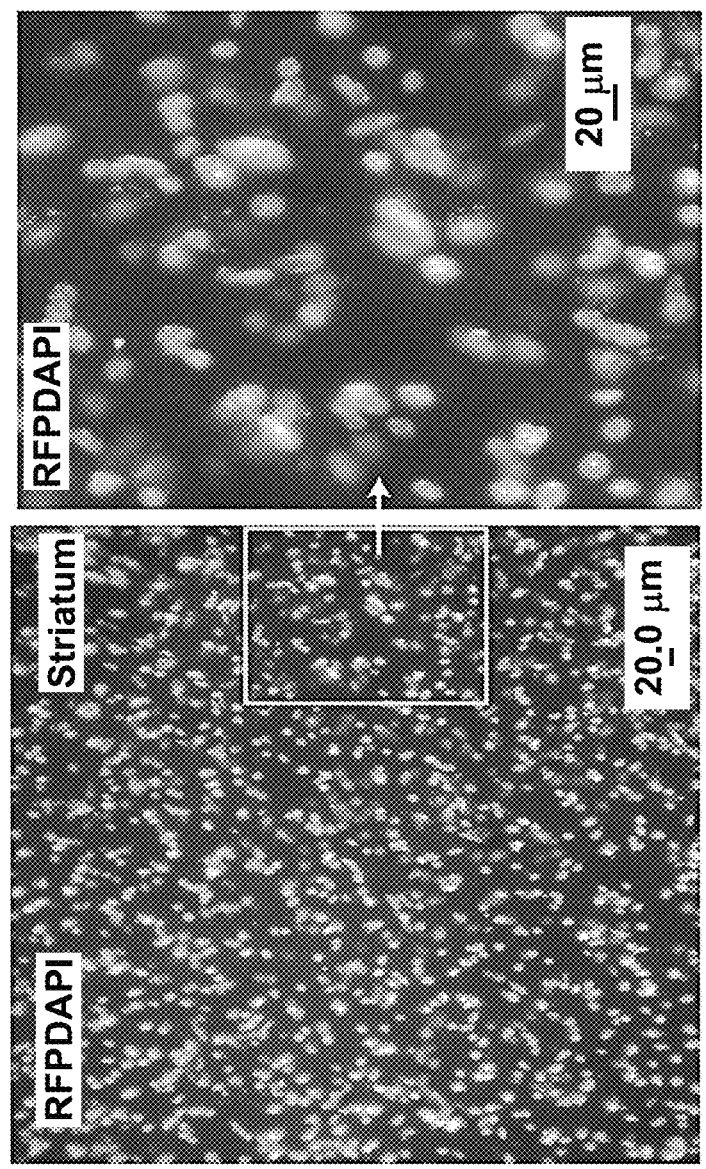

FIG. 3D illustrates the ventral striatum. Left panel: DAPI-stained nuclei and RFP expression; Right panel: magnified yellow box from panel on left shows RFP expression in cytoplasm distributed in a perinuclear pattern in many, but not all cells.

Figure 4:
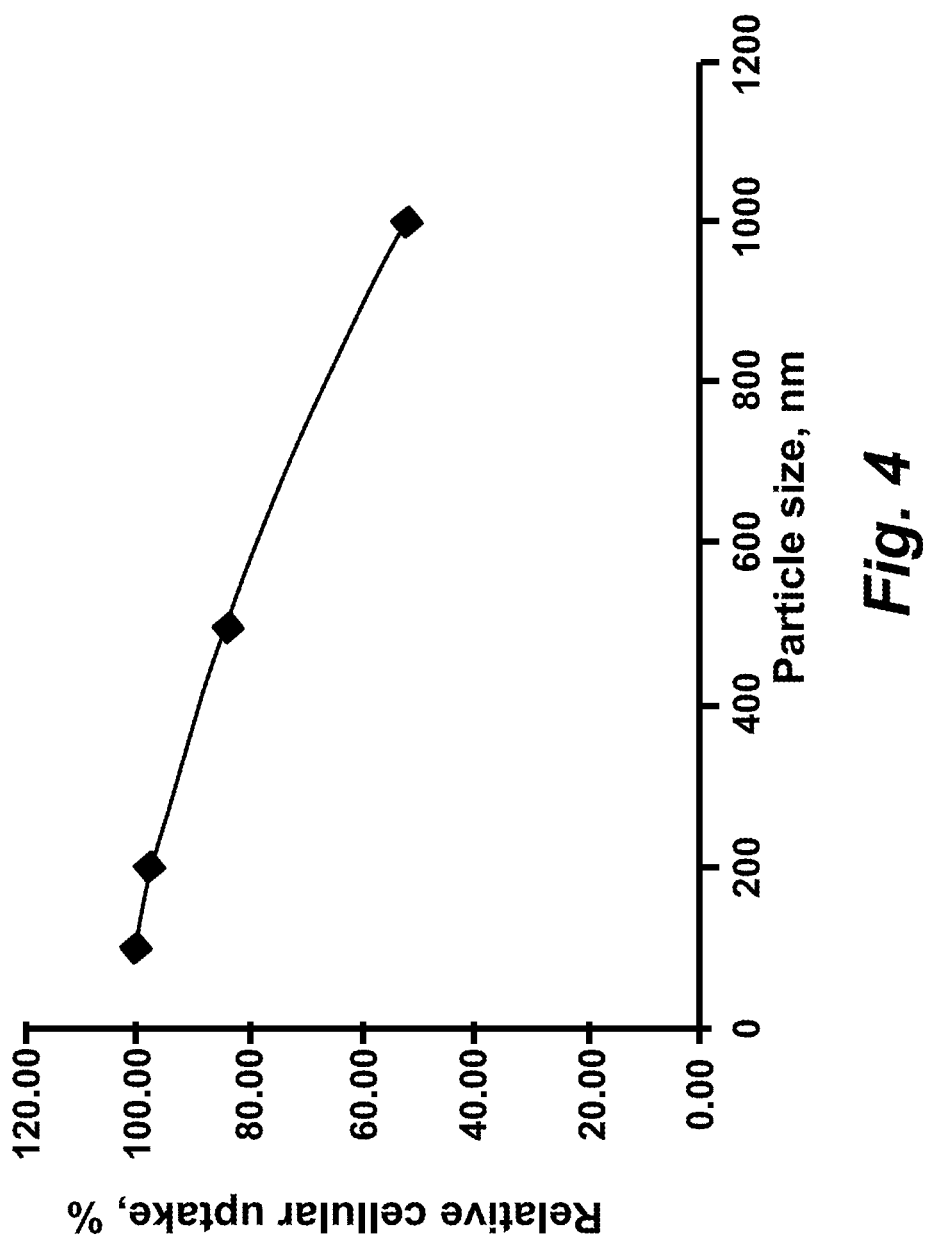

FIG. 4 is a graph illustrating the dependence of cellular uptake on nanoparticle size (Wn & Feng, (2005) *Biomaterials* 26: 2713-2722).

Figure 5:
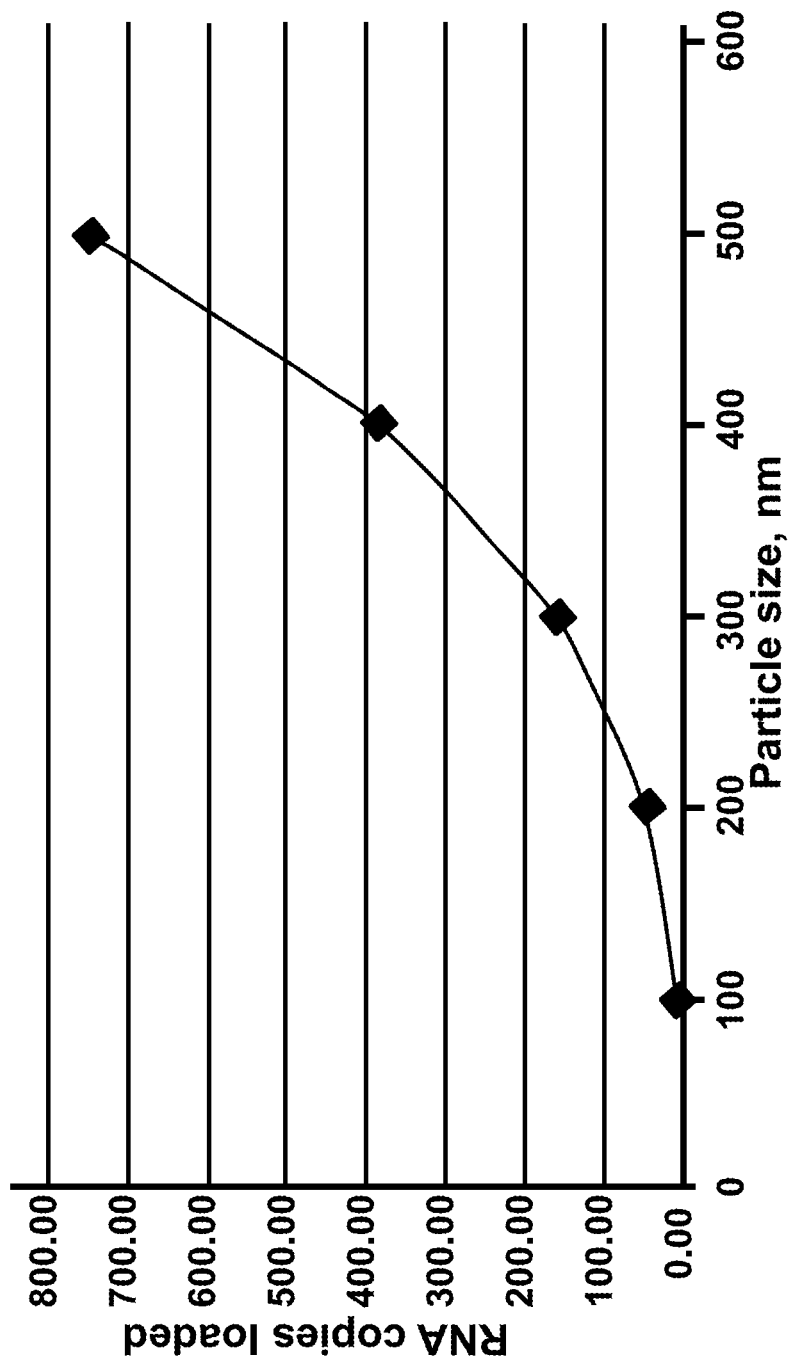

FIG. 5 is a graph illustrating the calculated loading capacity of nanoparticles depending on size.

Figure 6:
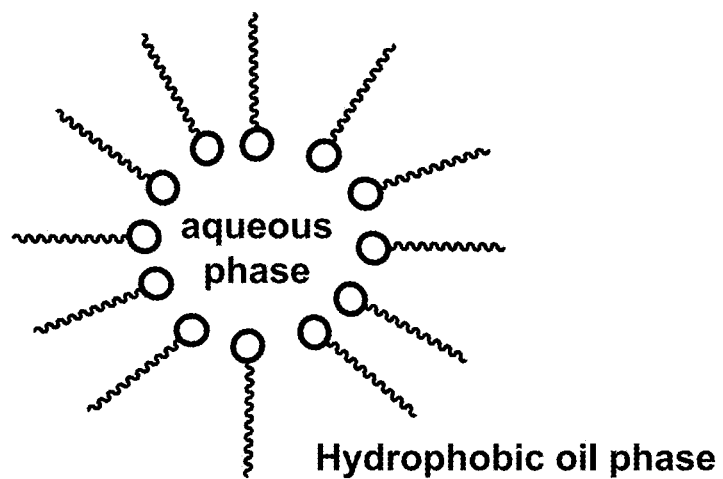

FIG. 6 illustrates a schematic representation of an inverse micelle used for micro-emulsion synthesis of nanoparticles.

Figure 7:
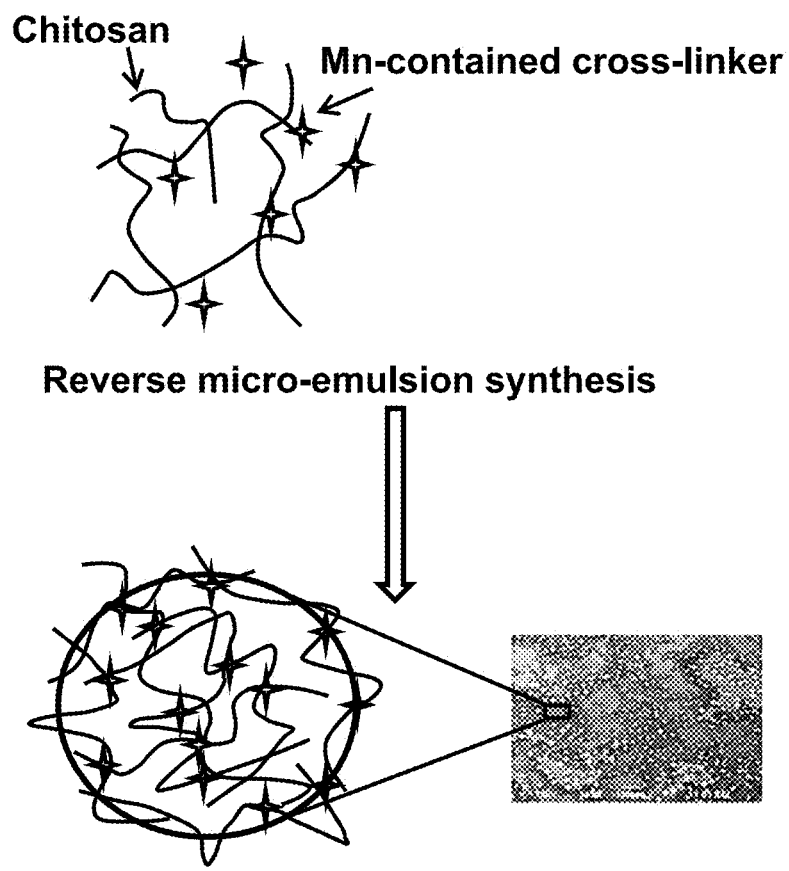

FIG. 7 illustrates the formation of the chitosan-based nanoparticles by reverse micro-emulsion synthesis.

Figure 8:
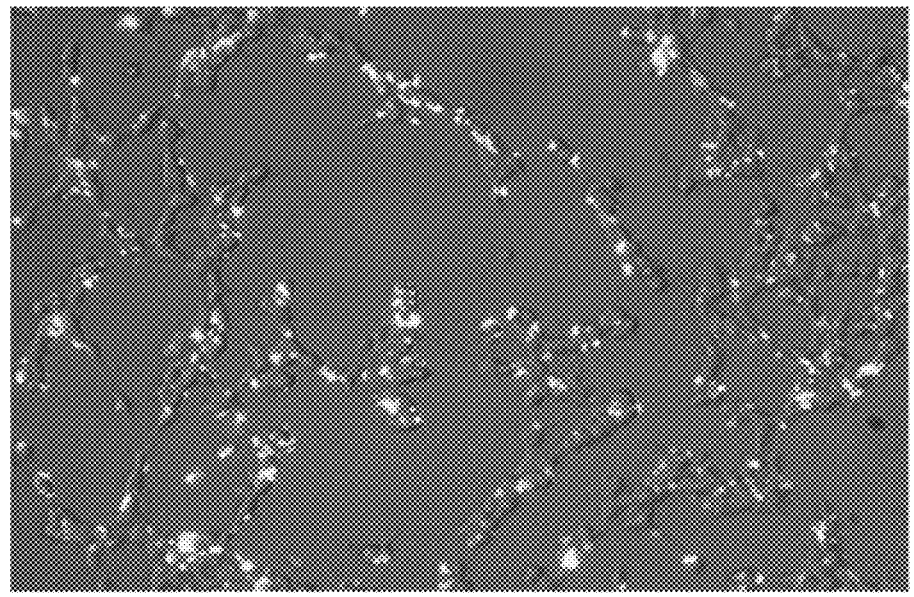

FIG. 8 is a digital photomicrograph of human SH5Y-SY neuroblastoma cells transfected with chitosan nanoparticles loaded with Alexa Fluor labeled dsRNA (Block-it Alexa Fluor , Invitrogen). Bright signal=fluorescent Alexa fluor dsRNA. Nanoparticles were fabricated by using low molecular weight chitosan (89 kDa) cross-linked with manganese-containing protoporphyrin IX. The concentration of nanoparticles was 10 µg/mL.

Figure 9:
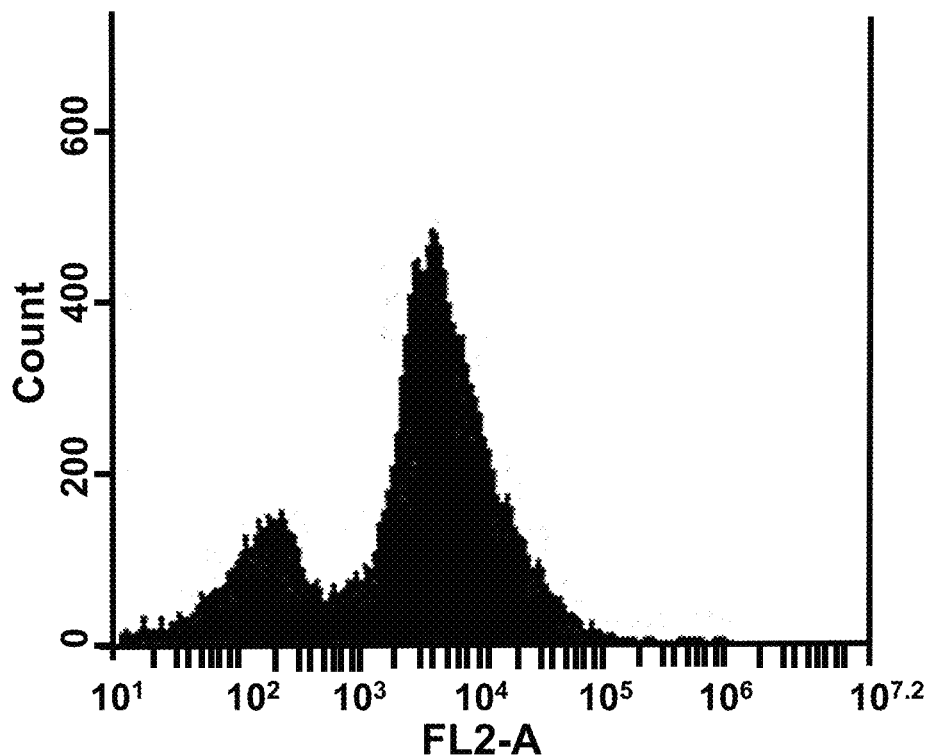

FIG. 9 illustrates a histogram representing populations of positive and negative cells transfected with chitosan nanoparticles loaded with red-labeled dsRNA to calculate transfection efficiency. The lower value fluorescence peak represents negative cells, and higher value fluorescence peak depicts positive cells.

Figure 10:
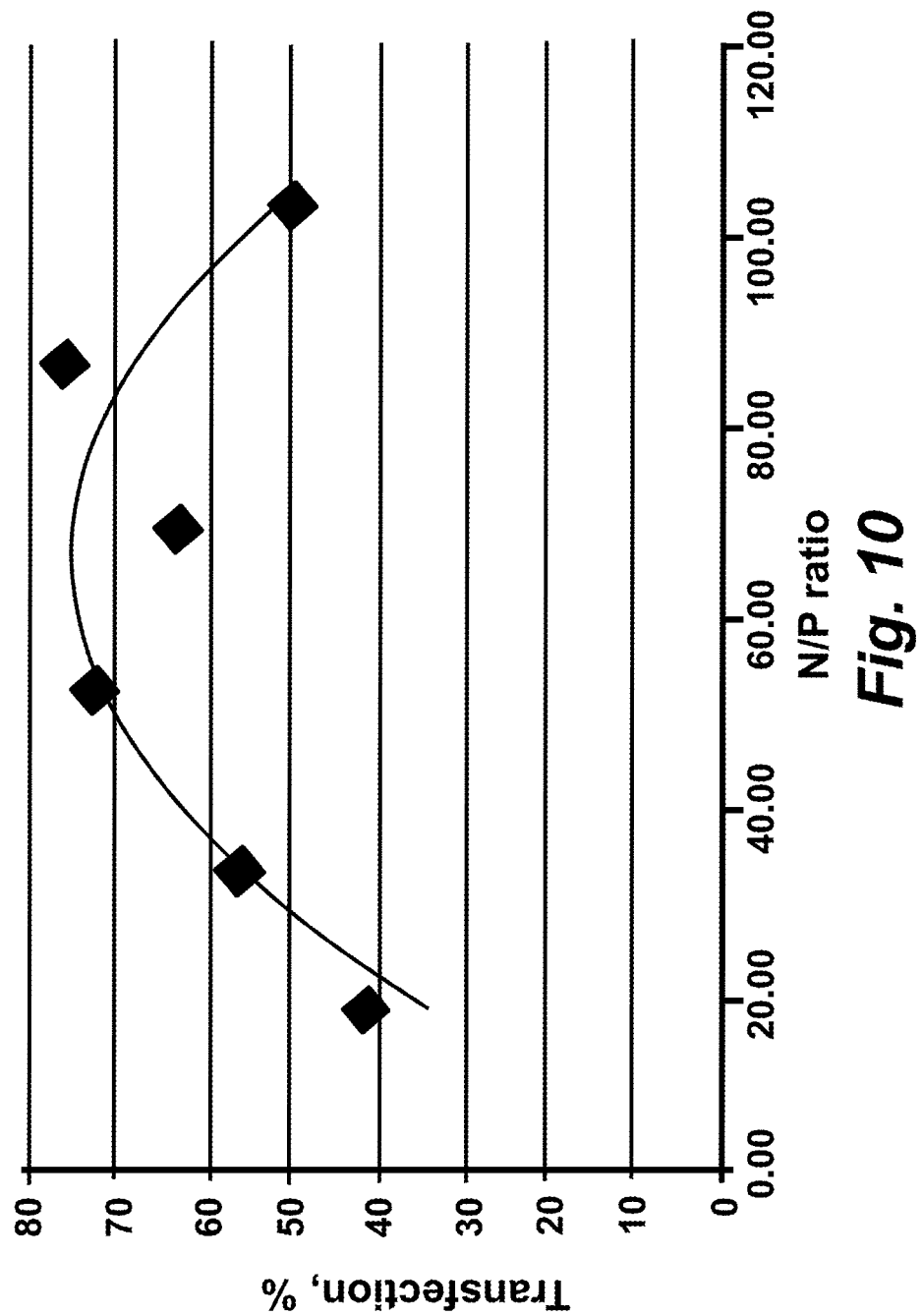

FIG. 10 is a graph illustrating the transfection efficiency for nanoparticle preparations 19-24 (Table 2) loaded with different amounts of dsRNA depicted as N/P ratio.

Figure 11:
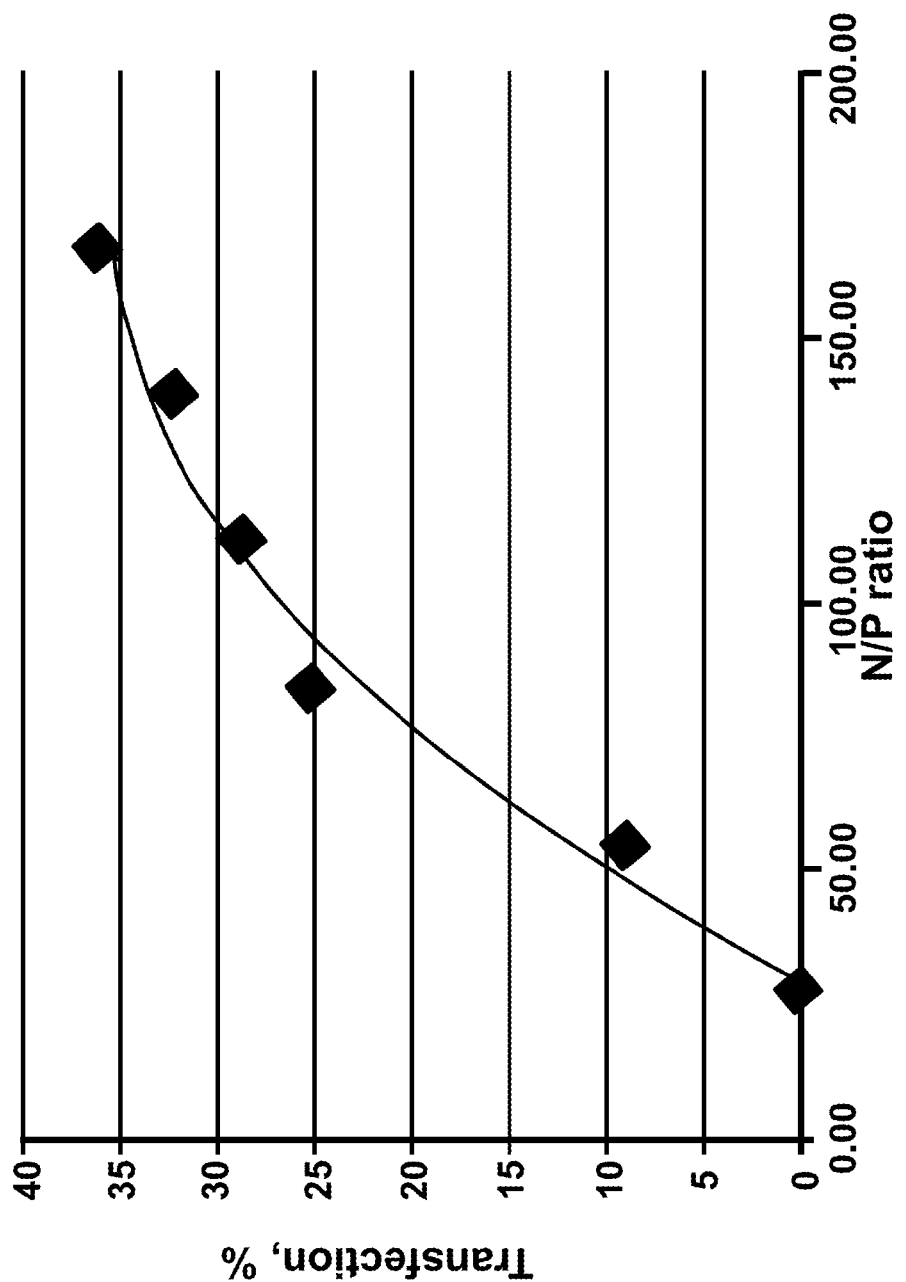

FIG. 11 is a graph illustrating the transfection efficiency in neuroblastoma cells for nanoparticle preparations 25-30 (Table 2) loaded with different amounts of dsRNA represented as N/P ratio.

Figure 12:
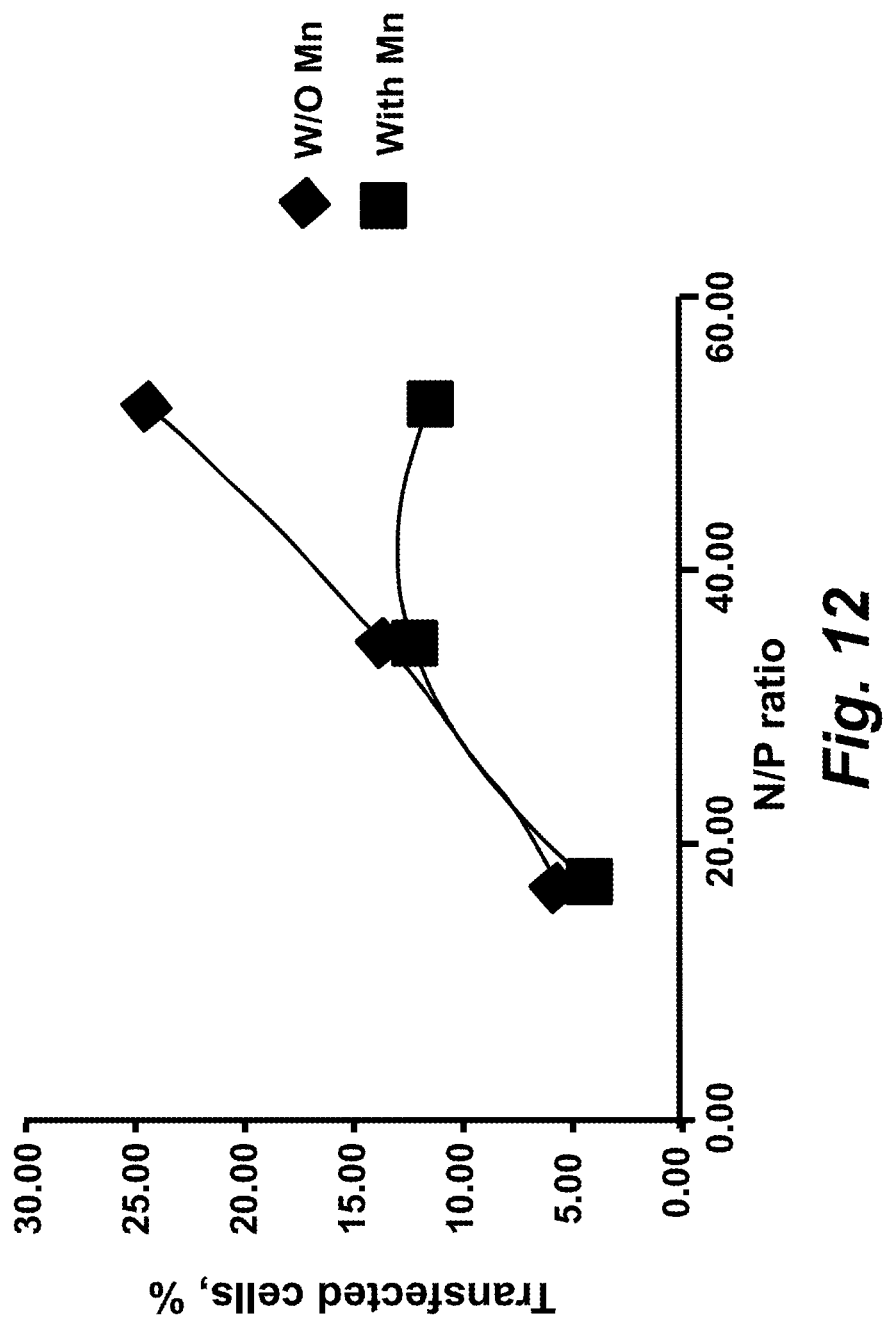

FIG. 12 is a graph illustrating the efficiency of transfection in neuroblastoma SH5Y-SY cells with dsRNA-loaded nanoparticles (preparations 13-18, Table 2) based on HM chitosan and EDTA as cross-linking agent.

Figure 13:
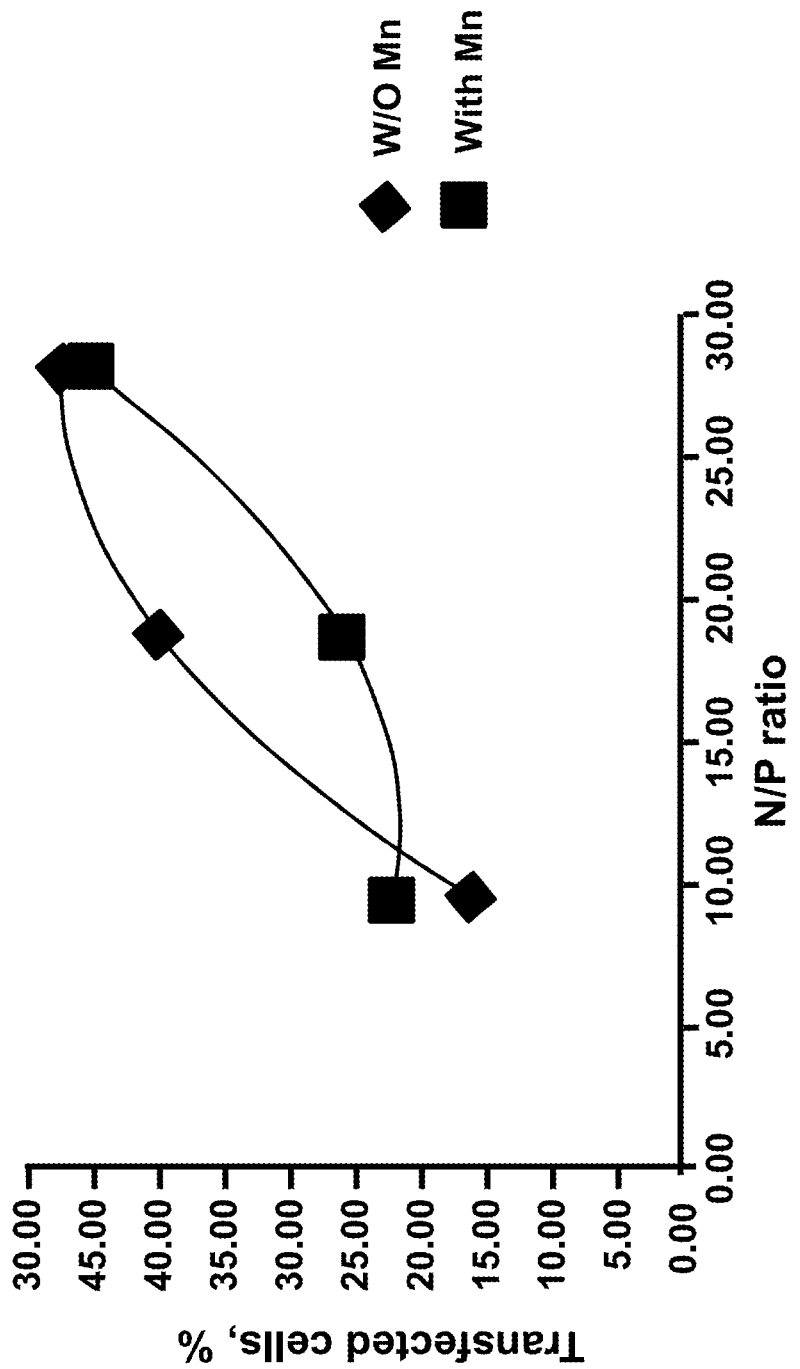

FIG. 13 is a graph illustrating the efficiency of transfection in neuroblastoma SH5Y-SY cells with dsRNA-loaded nanoparticles (preparations 6-11, Table 2) based on LM chitosan and EDTA as cross-linking agent.

Figure 14:
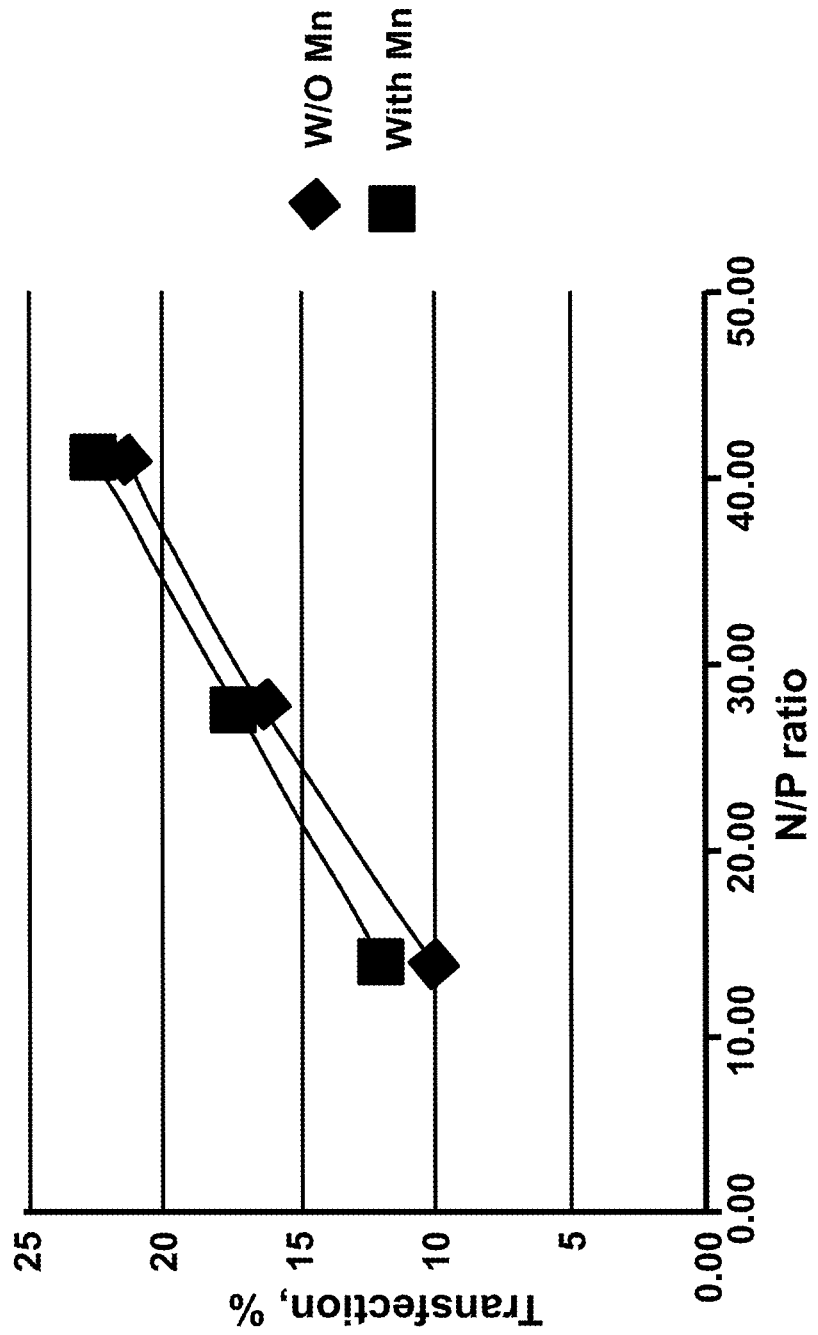

FIG. 14 is a graph illustrating the transfection efficiency for nanoparticle preparations 31-36 (Table 2) loaded with different amounts of dsRNA represented as N/P ratio in relationship with presence of manganese in HM chitosan nanoparticle fabricated with an EDTRA cross-linker.

Figure 15:
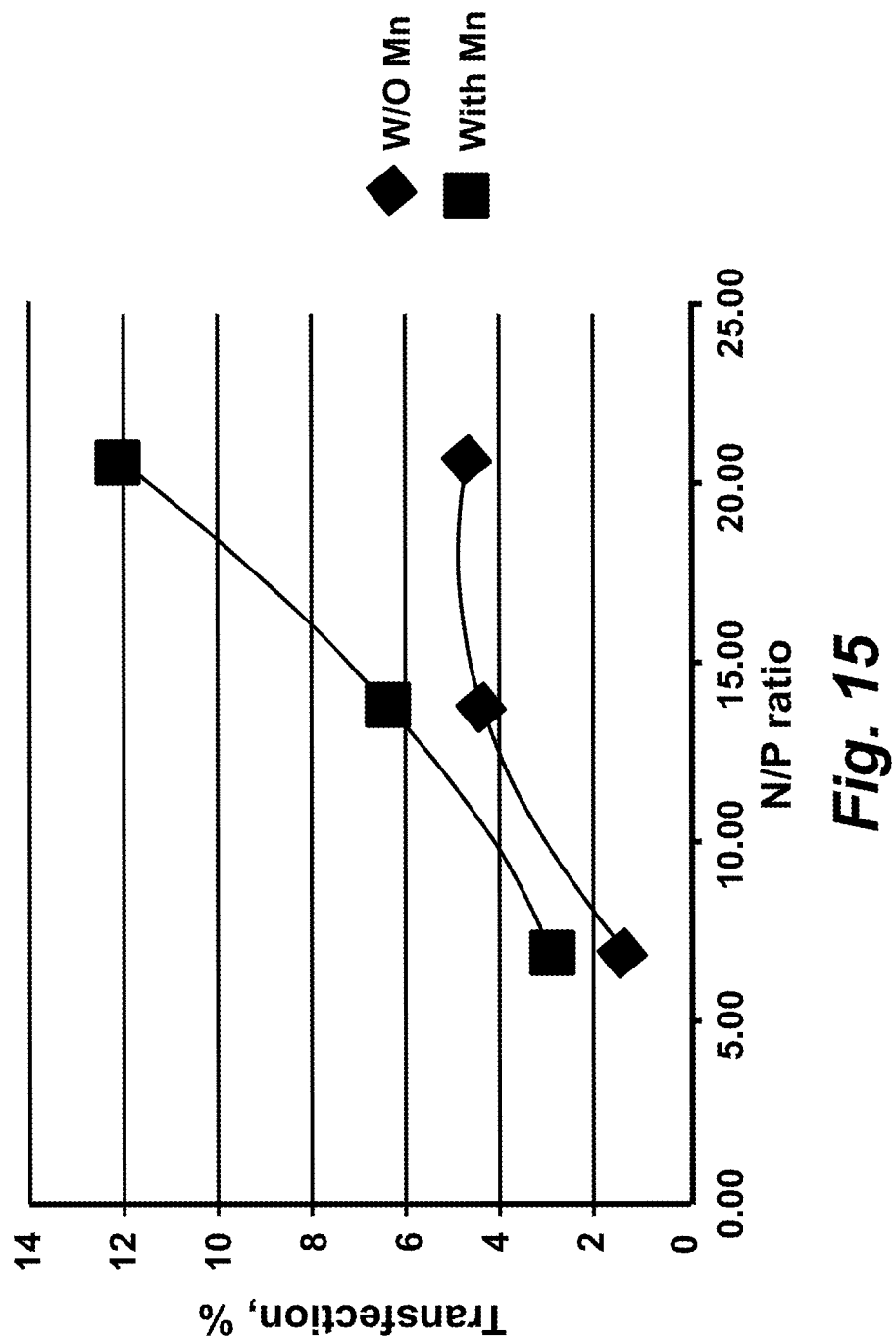

FIG. 15 is a graph illustrating the transfection efficiency for nanoparticle preparations 37-42 (Table 2) loaded with different amounts of RNA represented as N/P ratio in relationship with presence of manganese in LM chitosan nanoparticle fabricated with EDTRA cross-linker.

Figure 16:
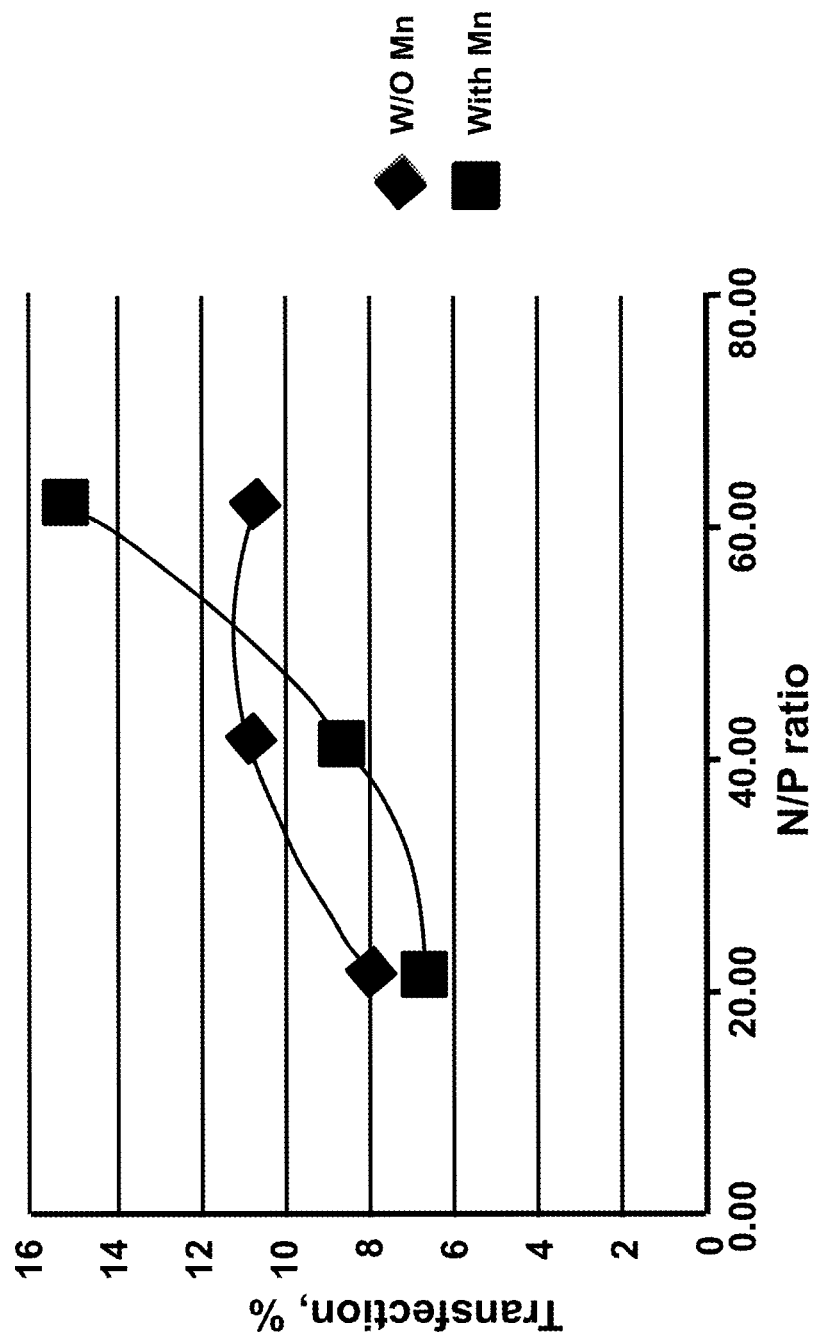

FIG. 16 is a graph illustrating the transfection efficiency for nanoparticle preparations 43-48 (Table 2) loaded with different amounts of dsRNA represented as N/P ratio in relationship with presence of manganese in NTAA as cross-linking agent.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean " includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Abbreviations

TA, L-(+)-Tartaric acid; EDTRA, Ethylenediamine-N,N;, N;-triacetic acid; PP, Protoporphyrin IX; NTAA, Nitrilotriacetic acid; MSA, Mercaptosuccinic acid; EDTA, Ethylenediaminetetraacetic acid Definitions The terms "core" or "nanoparticle core" as used herein refers to the inner portion of nanoparticle. A core can substantially include a single homogeneous monoatomic or polyatomic material. A core can be crystalline, polycrystalline, or amorphous. A core may be "defect" free or contain a range of defect densities. In this case, "defect" can refer to any crystal stacking error, vacancy, insertion, or impurity entity (e.g., a dopant) placed within the material forming the core. Impurities can be atomic or molecular.

While a core may herein be sometimes referred to as "crystalline", it will be understood by one of ordinary skill in the art that the surface of the core may be polycrystalline or amorphous and that this non-crystalline surface may extend a measurable depth within the core. The core-surface region optionally contains defects. The core-surface region will preferably range in depth between one and five atomic-layers and may be substantially homogeneous, substantially inhomogeneous, or continuously varying as a function of position within the core-surface region.

Chelating agents containing paramagnetic metals for use in magnetic resonance imaging can also be employed as ancillary agents. Typically, a chelating agent containing a paramagnetic metal is associated with a coating on the nanoparticles. The chelating agent can be coupled directly to one or more of components of the coating layer, such as a polyaspartate coat. Suitable chelating agents include a variety of multi-dentate compounds including EDTA, DPTA, DOTA, and the like. These chelating agents can be coupled directly to functional amino groups of a polyaspartate coat of the nanoparticles. The term "nanoparticle" as used herein refers to a particle having a diameter of between about 1 and about 1000 nm. Similarly, by the term "nanoparticles" is meant a plurality of particles having an average diameter of between about 1 and about 1000 nm.

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "contacting a cell or population of cells" as used herein refers to delivering a probe according to the present disclosure to an isolated or cultured cell or population of cells, or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading into a target organ or tissue such as a prostate, and so reducing dilution of the probe in the general circulatory system.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "bioluminescence" as used herein refers to a type of chemiluminescent, emission of light by biological molecules, particularly proteins. The essential condition for bioluminescence is molecular oxygen, either bound or free in the presence of an oxygenase, a luciferase, which acts on a substrate, a luciferin in the presence of molecular oxygen and transforms the substrate to an excited state, which upon return to a lower energy level releases the energy in the form of light.

The term "luciferase" as used herein refers to oxygenases that catalyze a light emitting reaction. For instance, bacterial luciferases catalyze the oxidation of flavin mononucleotide and aliphatic aldehydes, which reaction produces light. Another class of luciferases, found among marine arthropods, catalyzes the oxidation of cypridina luciferin, and another class of luciferases catalyzes the oxidation of coleoptera luciferin. Thus, "luciferase" refers to an enzyme or photoprotein that catalyzes a bioluminescent reaction. The luciferases such as firefly and *Renilla* luciferases are enzymes that act catalytically and are unchanged during the bioluminescence generating reaction. The luciferase photoproteins, such as the aequorin and obelin photoproteins to which luciferin is non-covalently bound, are changed by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known. Reference, for example, to "*Renilla* luciferase" means an enzyme isolated from member of the genus *Renilla* or an equivalent molecule obtained from any other source, such as from another Anthozoa, or that has been prepared synthetically.

The term "polypeptide" as used herein refers to proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

Description

The compositions and methods of the disclosure particularly target the divalent metal transporter expressed on olfactory nerve terminals to transport divalent cation-coated or cation-containing nanoparticles to all regions of brain. It has been found that such divalent cation-containing containing nanoparticles, including those nanoparticles comprising manganese as in the form of, but not limited to, manganese oxide have affinity for the metal transport receptor proteins. Although this receptor has particular affinity for manganese, it is contemplated that other divalent ions, including magnesium, calcium, and the like may also be bound to such receptors leading to transport of the nanoparticles into the intracellular cytoplasm.

Nanoparticles have been developed as a vehicle for parenteral delivery of genes, proteins and drugs. The present disclosure encompasses embodiments of nanoparticle-based compositions and methods for the use thereof for the delivery of genes, oligonucleotides, including but not limited to small interfering RNA, and other small molecule drugs, into the brain by nasal insufflation.

It is contemplated that in some embodiments, the nanoparticles can be made of chitosan or other biological-compatible polymer and provides a way to deliver the nanoparticle to the brain via the olfactory nerve terminals of the nasal epithelium, Therefore, for example, instillation of the manganese oxide-coated nanoparticles (in aqueous solution) into the nasal cavity or insufflation of the nanoparticles in suspension can deliver the gene or other compatible product of interest into the CNS.

The nanoparticles of the disclosure can take advantage of the capacity of manganese (or other divalent cations) to be taken up by nerve terminals by means of the bivalent metal transporter of the olfactory nerves, and hence to be transported to the olfactory bulb and from there, via transynaptic mechanisms to the entire brain.

The compositions and methods of the disclosure are also advantageous for the ability to visualize the uptake of the nanoparticle into brain by MRI because of the characteristics, particularly of manganese, which result in increased signal in T-1 weighted MR images (Na et al., (2007) *Angew. Chem. Int Ed* 46: 5397-540).

The invention addresses the problem of delivery of specific therapeutic genes, gene products and small interfering RNA (siRNA) into brain without neurosurgical intervention and without the requirement of viral vectors and the delivery of other small molecules that may have difficulty in crossing the blood-brain barrier.

The divalent metal transporter expressed by olfactory nerve terminals of the olfactory epithelium actively take up the manganese-coated nanoparticles (NP) into the olfactory bulb. The trans-synaptic transfer of the nanoparticle from olfactory cortex to other regions of brain, especially to basal ganglia can occur readily and is dependent on the concentration of the nanoparticle in the olfactory bulb. Within cells, the nanoparticle can then release the nucleic acid, leading to the expression of the gene or modulation of a gene activity by such as a gene-silencing RNA of interest. The free manganese, for example, can be eliminated from brain rapidly by homeostatic mechanisms that keep tissue levels of the metal within a very narrow range.

The advantage of this method of gene or drug delivery is that, for example, manganese-coated nanoparticles can be visualized by MRI T-1 weighted images, thereby obtaining an in vivo measure of the time-course of nanoparticle distribution in the recipient subject.

The present disclosure encompasses embodiments of a nanoparticle delivery vehicle having a divalent metal available for binding to cell surface receptors such as those found on olfactory cells of the olfactory epithelium, and methods of administering a therapeutic agent to a recipient subject by using said nanoparticles. In embodiments of the delivery vehicles of the disclosure, a nanoparticle comprises a nanoparticle core having a divalent metal, metal ion, or metal oxide embedded in the core or disposed on the surface of the core. In the latter case, it is contemplated that the divalent metal or derivatives thereof may be held on the surface of the core by ionic forces between the core and the metal, or there is an intermediary that links the metal to the core. For example, but not intended to be limiting, a chelating agent may be bonded to an underlying nanoparticle and hence available to bond to metal ions or metallic particles or oxides. Suitable chelators include, but are not limited to, such as ethylenediamine tetaraacetic acid (EDTA), ethylene glycol tetraacetic acid (EGTA), citrate, and the like. Table 1 illustrates representative examples of suitable cross-linker chelators useful for incorporation into the nanoparticles of the disclosure.

In the nanoparticles of the present disclosure, the core may comprise any pharmaceutically acceptable material that may form nanoparticles. During the process of the formation of the nanoparticles the core material may be mixed with the agent desired to be delivered to the neural tissue of a recipient animal or human subject so that the agent is embedded in the body of the nanoparticle core and not just disposed on the outer surface of the core. For example, but not intended to be limiting, an advantageous nanoparticle suitable for delivery of an agent to the olfactory tissue receptors can comprise chitosan or a modified chitosan such a s a thiolated chotisan, to which may be attached a nucleic acid by electrostatic binding (see also Wang et al., (2011) *Int. J. Nanomed.* 6: 765-774, incorporated herein by reference in its entirety). In some embodiments, the nanoparticles may comprise a biocompatible protective coat such as a polyethylene glycol coat. The embodiments of the nanoparticles of the disclosure may further comprise a cross-linker for cross-linking individual chitosan moieties. Such cross-linkers may further be able to chelate divalent metals. In other embodiments, chelators may be attached to the nanoparticle or the protective coat thereof, thereby binding divalent metals to the surface of the nanoparticles as wells as, or instead of be integral to the structure of the nanoparticle core. It is also within the scope of the disclosure for an agent desired to be delivered to the brain of a recipient animal or human subject to be linked directly or indirectly to the core material by covalent or electrostatic bonds that allow the agent to be bioactively available once delivered to the cells of the central nervous system.

The nanoparticles for use as delivery vehicles according to the present disclosure may further comprise one or more coats that partially or totally envelop the nanoparticles and may confer on the particles properties such as biocompatibility, enhanced affinity for cell surface components, or form a substratum for the attachment of one or more bioactive agents, and particularly for the attachment of a divalent metal, metal ions, or metal oxide. For example, but not intended to be limiting, a coat or layer of polyethylene glycol may be disposed on the outer surface of a nanoparticle core that itself comprises the agent to be delivered to the central nervous system of the recipient animal or human subject. The addition of such a coat, however, can mask the availability of the divalent metal for binding of the nanoparticle to a recipient cell or receptor thereof. Accordingly, it is contemplated that a linker may be included within, on, or bonded to, the biocompatible coat whereby a divalent metal, metal ion, or oxide, as individual ions or as nanoparticles thereof, may be attached to the coated nanoparticle delivery vehicle. For example, but not intended to be limiting, poly-L-histidine peptides may be incorporated into the nanoparticle coating. Such a peptide has the ability to bind to divalent cations by electrostatic bonds and therefore act as a linker between the ions and the coating layer.

Coatings applied to the outer surface of a nanoparticle core according to the present disclosure may further be used to attach such molecules as imaging agents, fluorphores and the like, antibodies that will specifically target the nanoparticles to a specific cell receptor or cell surface molecule or to attach to the delivery vehicle the agent desired to be delivered to the CNS of the recipient subject.

The nanoparticle deliver vehicles of the present disclosure may incorporate any divalent metal that may have affinity for a metal transporter receptor found on the surface of the olfactory cells of the nasal epithelium. Preferably, the divalent metal is pharmaceutically acceptable to the recipient subject, particularly upon prolonged exposure thereto. Thus, advantageous divalent metals for use in the compositions of the present disclosure include iron, cobalt, nickel, copper, lead, cadmium, calcium, magnesium, and manganese. Especially advantageous is the use of manganese that has been shown to be able to be readily bound to the metal transporter receptor and be efficiently transported to the intracellular milieu of olfactory cells. Following the uptake by such cells, manganese is transported to the olfactory bulb and hence into the tissues of the central nervous system. Although not intended to be limiting, it has been shown that a suitable form of manganese for attachment to the nanoparticle delivery vehicles herein disclosed are manganese oxide nanoparticles having diameters of between about 5 to about 7 nanometers and which may, for example, be bound by poly-L-histidine peptides.

Upon binding to a surface receptors, the nanoparticles of the disclosure can be internalized into the olfactory cells and transported to the olfactory bulb of the central nervous system, and hence to other regions of the brain. Accordingly, the delivery vehicles of the disclosure are able to transfer compositions into neural tissue, and especially into the tissues of the brain by by-passing the blood-brain barrier that would otherwise provide an obstruction to the delivery of molecules via the vascular system routes of administration.

The nanoparticles themselves may be any nanoparticle that it is desired to be delivered to the brain tissues of an animal or human subject. Such nanoparticles may be, for example, but not intended to be limiting, metallic nanoparticles or quantum dots useful for imaging by techniques such as CT scanning, MRI, PET scanning, fluorescence-based scanning and the like. The nanoparticles may contain a therapeutic agent such as, but not limited to, a cell growth inhibitor or modulator, a drug to modulate a biochemical or physiological process of the brain, a modulator of the neural activity of the brain or central nervous system of the recipient, or a nucleic acid intended to modify the genetic composition of neural cells or to modulate the activity or expression of a gene of a neural cell. It is contemplated, therefore, that the delivery vehicles of the present disclosure are useful for the delivery of any pharmaceutically acceptable compound that may be desired to be delivered to the central nervous tissue At a sufficient nitrogen to phosphate (N/P) charge ratio, chitosan can condense siRNA to sizes compatible with cellular uptake while efficiently preventing nucleases from accessing the enclosed nucleic acid drugs by steric protection (Huang et al., (2005) *J. Control. Release* 106: 391-406). However, a strong electrostatic charge can prevent siRNA release at the site of action; therefore, a balance needs to be achieved by adjusting formulation-related parameters. The molecular weight of chitosan is a factor that influences particle size, complex stability, the efficiency of cell uptake, the dissociation of DNA from the complex after endocytosis and, therefore, the transfection efficiency of the complex (Sato et al., (2001) *Biomaterials* 22: 2075-2080; MacLaughlin et al., (1998) *J. Control. Release* 56: 259-272). The size of complexes has been shown to decrease as the molecular weight of the chitosan is decreased (MacLaughlin et al., (1998) *J. Control. Release* 56: 259-272). However, a further decrease of the molecular weight reversed the tendency. Therefore, the appropriate molecular weight should be selected to achieve the desirable particle size because the transfection efficiency of the cationically modified particles depends strongly on the size of the particles, which determines their cellular uptake (Nafee et al., (2007) *Nanomedicine: Nanotechnol. Biol. Med.* 3: 173-183).

The present application encompasses embodiments of chitosan-based formulations for the delivery of a nucleic acid such as, but not limited to, an siRNA into brain by using a non-invasive route based on intranasal instillation. Incorporation of manganese into the structure of the nanoparticle surface harnesses the capacity of divalent metal transporters located on olfactory nerve terminals to actively take-up and deliver the nanoparticles into specific regions of brain.

Three grades of chitosan were used to manufacture and test the nanoparticles according to the present disclosure, including a low molecular (LM) preparation with about 60 to about 90 kDA and a high molecular (HM) preparation of chitosan with about 400 kDA average molecular weight.

The most important factor influencing cellular uptake of nanoparticles is the particle size. FIG. 4 demonstrates the dependence of cellular uptake on particle size. There was about a 2-fold decrease in transfection efficiency for particles of about 1000 nm size.

The siRNA loading capacity of the nanoparticles was calculated as a function of size. As shown in FIG. 5, the larger nanoparticles allowed higher amounts of RNA copies to be loaded into each nanoparticle. However, large-sized nanoparticles (when they become comparable with the size of cells) are limited because of poor cellular uptake, as demonstrated in FIG. 4. The very small nanoparticles, as indicated in FIG. 5, are limited because of low loading capacity. Thus, enhancement of transfection efficiency required optimization of nanoparticle size.

Among the current methods for nanoparticle fabrication, reverse micro-emulsion synthesis advantageously permits a narrow size distribution of less than about 100 nm and it allows control of the size of the final nanoparticles (Sunil et al., (2004) *J. Controlled Release* 100: 5-28).

FIG. 6 schematically illustrates a structure of an inverse micelle that can serve as a chemical reactor for the synthesis of nanoparticles according to the disclosure. Inverse micelles have the head groups (such as chitosan) at the center with the tails extending outwards (water-in-oil micelle). The chitosan is present in the aqueous phase of the micelle together with a selected cross-linker that covalently links the macromolecules of chitosan to create rigid spherical structures with the size of micro-emulsion micelles. The flow chart shown in FIG. 4 illustrates the method of synthesis of chitosan nanoparticles of the disclosure. It includes cross-linking agents that can incorporate metal, for instance manganese, into the formed structure of the nanoparticles. Exemplary cross-linkers for use in the manufacture of the nanoparticles of the disclosure are shown, but not limited to, those in Table 1

TABLE 1

Chemical structures of crosslinking agents used for chitosan nanoparticles preparation.

| Acronym | Chemical Name | Chemical structure |
|---------|---------------|--------------------|
| TA | L-(+)-Tartaric acid | 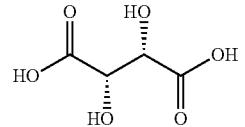 |

TABLE 1-continued

Chemical structures of crosslinking agents used for chitosan nanoparticles preparation.

| Acronym | Chemical Name | Chemical structure |
|---------|---------------|---------------------|
| EDTRA | Ethylenediamine-N,N;,N;-triacetic acid | 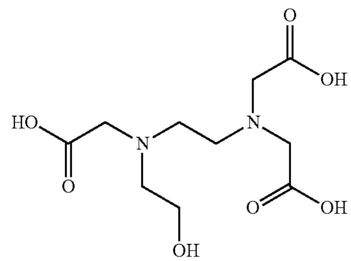 [SMILES: O=C(O)CN(CCO)CCN(CC(=O)O)CC(=O)O] |
| PP | Protoporphyrin IX | 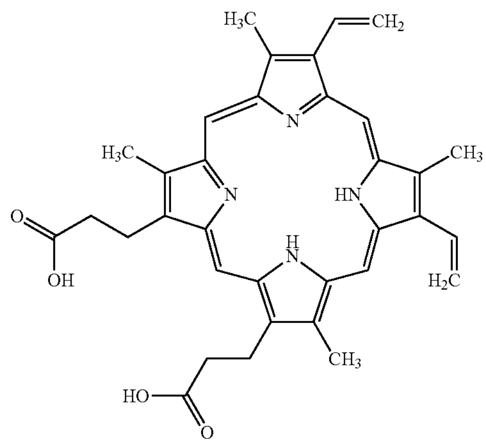 [SMILES: C=CC1=C(C)c2cc3nc(cc4[nH]c(cc5[nH]c(cc1n2)c(C)c5C=C)c(C)c4CCC(=O)O)C(CCC(=O)O)=C3C] |
| NTAA | Nitrilotriacetic acid | 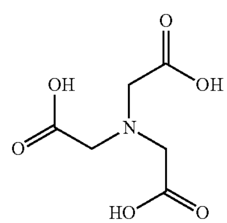 [SMILES: O=C(O)CN(CC(=O)O)CC(=O)O] |
| MSA | Mercaptosuccinic acid | 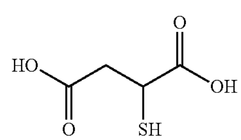 |
| EDTA | Ethylenediaminetetraacetic acid | 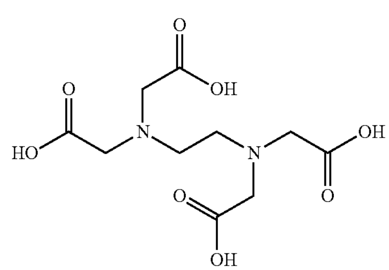 [SMILES: O=C(O)CN(CCN(CC(=O)O)CC(=O)O)CC(=O)O] |

Figure 1:
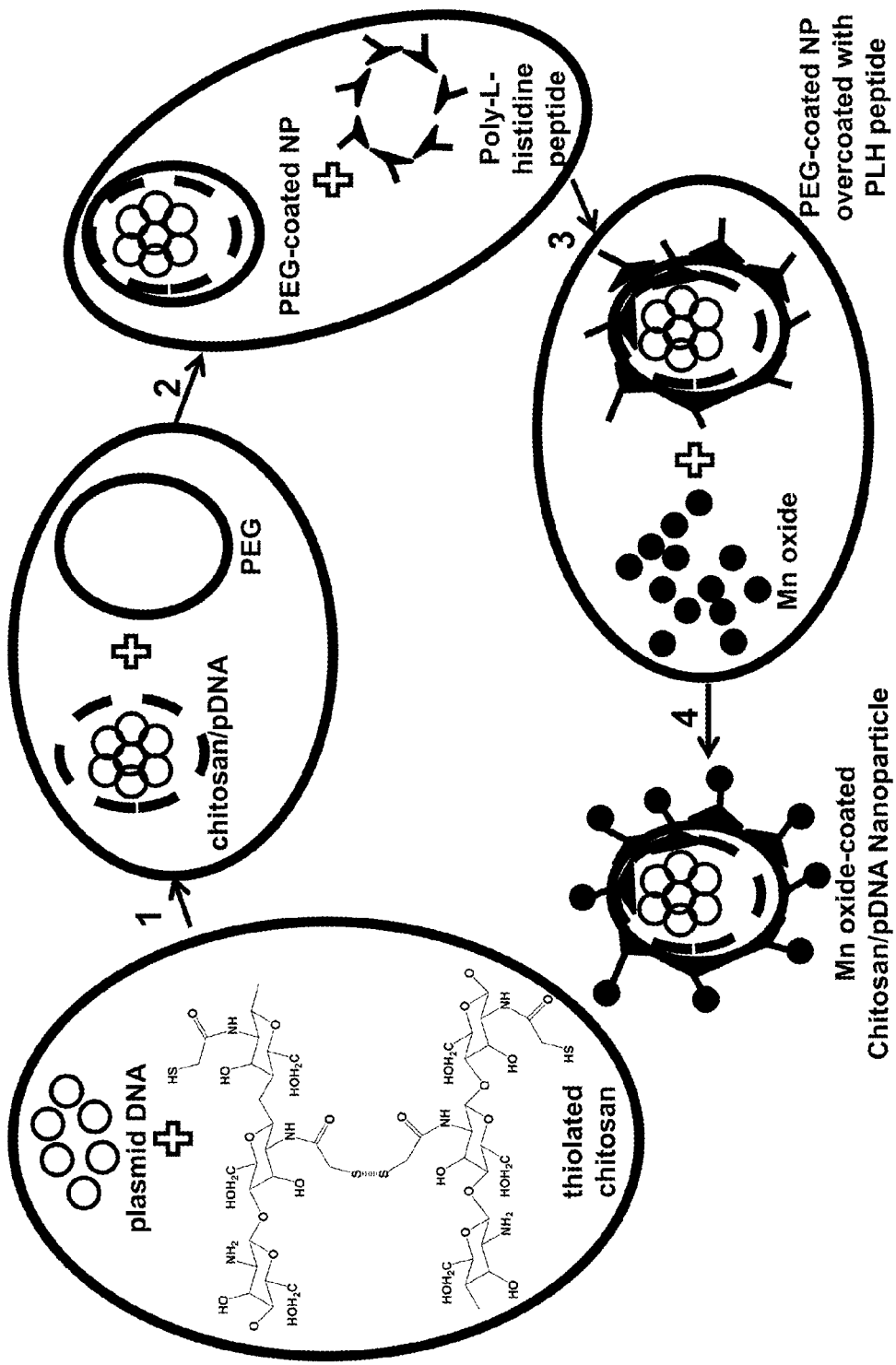
FIG. 1 schematically illustrates a manganese oxide-coated chitosanipDNA nanoparticle.
Figure 2:
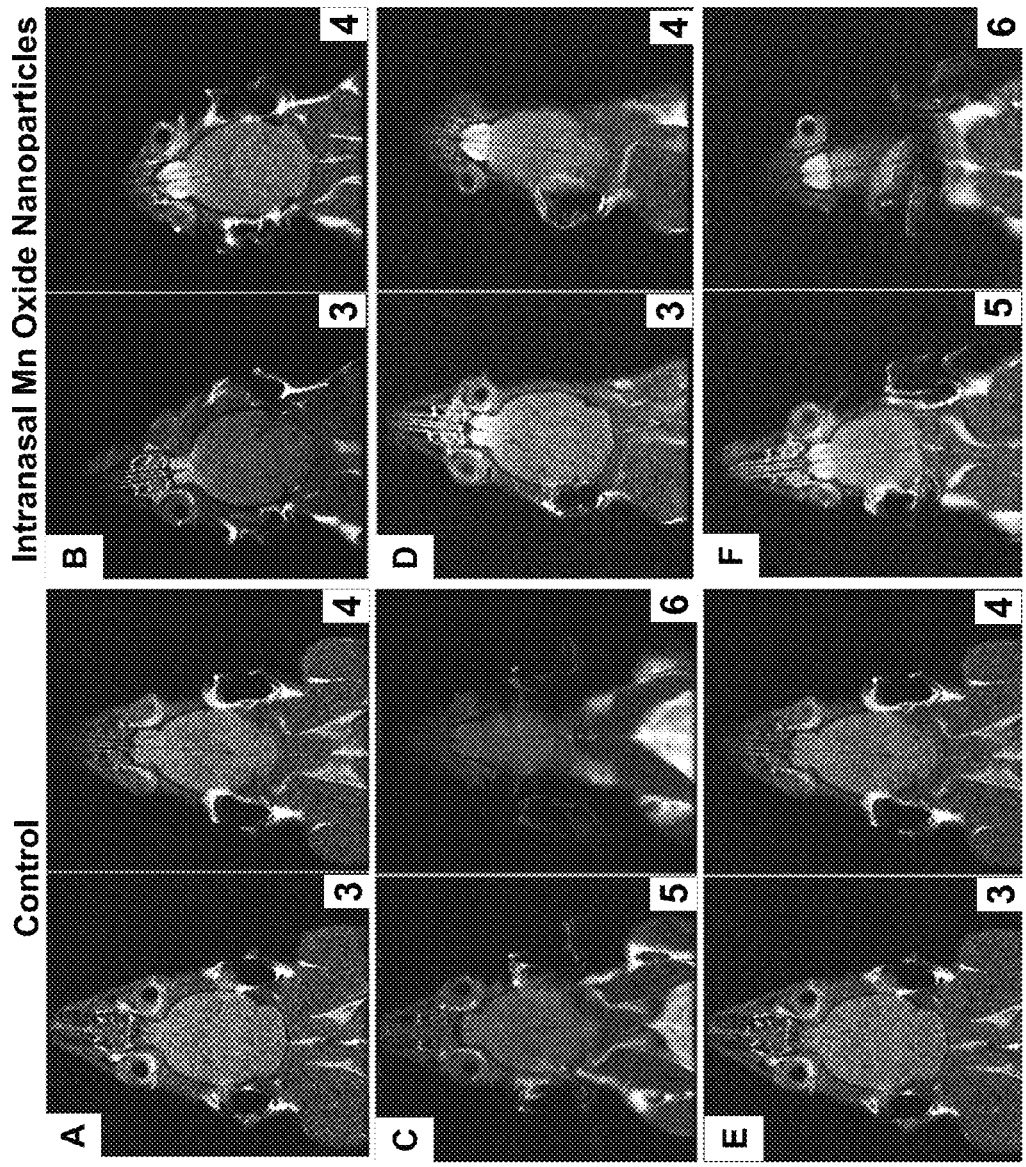
FIG. 2 illustrates digital images from micro-bore MRI of mice following intranasal instillation of a Manganese-containing nanoparticle. Animal in panels A, C, and E received vehicle alone, and animal in panels B, D, and E received the Manganese-containing nanoparticle. Time: 7 days after administration of the nanoparticles. Highest intensity of signal is in olfactory bulbs. Signal intensity is also higher in cortical regions of brain in the manganese-treated mice than in vehicle control-treated mice.

One embodiment of the nanoparticle of the disclosure is illustrated in FIG. 1. Other embodiments include the distribution of manganese or manganese oxide (in proportions with the chitosan/DNA of about 1 to about 1; about 1 to about 2; about 1 to about 4; about 1 to about 8). It is contemplated that the metallic oxide may be embedded within the nanoparticle with at least some of the metallic compound exposed at the outer surface of the nanoparticle for binding to a receptor of the targeted olfactory cell, or most advantageously attached to the outer surface of the nanoparticle by a chelating linker.

Accordingly, the incorporation of manganese into the structure of chitosan-based nanoparticles resulted in either increased or decreased transfection efficiency depending on the molecular weight of chitosan and the structure of cross-linking agents used. It has been shown that nanoparticles fabricated on LM chitosan manganese can be used to enhance transfection efficiency in a human neuronal cell line. However, for some other cross-linkers lacking chelation capacity, the transfection efficiency was sufficient for application even without incorporation of manganese, but experiments with manganese-containing nanoparticles showed the transport of the manganese-containing nanoparticle from nasal epithelium into the olfactory bulb and other regions of brain and expression of the DNA payload (red fluorescent protein) in olfactory bulb and other regions of the recipient mouse brain. Additionally, it has been shown that manganese-containing chitosan-based nanoparticles carry siRNA directed against green fluorescent protein (GFP) to study transport from olfactory epithelium into brain of transgenic GFP mice.

One aspect of the present disclosure, therefore, encompasses embodiments of a method of delivering a therapeutic agent via an olfactory nerve to the central nervous system (CNS) of an animal or human subject, the method comprising administering to the nasal epithelium of the animal or human subject a pharmaceutically acceptable composition comprising a nanoparticle delivery vehicle, where the nanoparticle delivery vehicle can comprise a nanoparticle core, a therapeutic agent desired to be delivered to the brain of a recipient subject, and a divalent metal having binding affinity for a divalent metal transporter of an olfactory nerve terminal, where the divalent metal can be a metal ion, a metal oxide, a metal ion nanoparticle, a metal oxide nanoparticle, or any combination thereof, where the divalent metal can be selected from manganese, magnesium, zinc, copper, nickel, iron, lead, cadmium, and calcium, whereupon the divalent metal can selectively binds to a divalent metal transporter of an olfactory nerve cell, and the nanoparticle delivery vehicle be internalized by said cell, migrating at least to the olfactory bulb of the CNS of the recipient animal or human subject.

In some embodiments of this aspect of the disclosure, the divalent metal is manganese.

In some embodiments of this aspect of the disclosure, the divalent metal when in the central nervous system of an animal or human subject can be detectable by imaging.

In some embodiments of this aspect of the disclosure, the nanoparticle core can comprise chitosan, a derivative thereof, or a polymerized chitosan or a derivative thereof.

In embodiments of this aspect of the disclosure, the nanoparticle core comprises chitosan, a derivative thereof, or a polymerized chitosan or a derivative thereof, and wherein said chitosan, the derivative thereof, the polymerized chitosan, or the derivative thereof, can be cross-linked by a cross-linker.

In embodiments of this aspect of the disclosure, the cross-linker can have bound thereto a metal divalent ion having affinity for a divalent metal transporter of an olfactory nerve cell.

In embodiments of this aspect of the disclosure, the nanoparticle can further comprise a biocompatible layer on the surface thereof.

In embodiments of this aspect of the disclosure, the biocompatible layer can further comprise a moiety having affinity for the divalent metal.

In embodiments of this aspect of the disclosure, the moiety having affinity for the divalent metal ion can be poly(L-histidine) or a chelating agent.

In embodiments of this aspect of the disclosure, the therapeutic agent to be delivered to the central nervous system of an animal or human subject can be selected from a nucleic acid, a protein, a peptide, a therapeutic agent, or a combination thereof, where the nucleic acid can be a single strand DNA, a double strand DNA, or an RNA, and where said nucleic acid can be selected from the group consisting of: an oligonucleotide, a vector comprising a nucleotide sequence desired to be expressed in a recipient cell of the central nervous system of an animal or human subject, an isolated nucleic acid, and a recombinant nucleic acid.

In embodiments of this aspect of the disclosure, the nucleic acid can be an siRNA.

In embodiments of this aspect of the disclosure, the method can further comprise the step of detecting the nanoparticle delivery vehicle in the recipient animal or human subject, thereby forming an image of the distribution of the nanoparticle delivery vehicle in a tissue of the central nervous system of an animal or human subject.

Another aspect of the disclosure encompasses embodiments of a nanoparticle delivery vehicle, the vehicle comprising: a nanoparticle core comprising chitosan, a derivative thereof, or a polymerized chitosan or a derivative thereof; and a divalent metal having binding affinity for a divalent metal transporter of an olfactory nerve terminal.

In embodiments of this aspect of the disclosure, the divalent metal can be disposed on the surface of the nanoparticle core.

In embodiments of this aspect of the disclosure, the divalent metal can be embedded in the nanoparticle core.

In embodiments of this aspect of the disclosure, the divalent metal can be a metal, a metal ion, a metal oxide, a metal ion nanoparticle, a metal oxide nanoparticle, or any combination thereof.

In embodiments of this aspect of the disclosure, the divalent metal can be selected from the group consisting of manganese, magnesium, zinc, iron, copper, nickel, lead, cadmium, and calcium.

In embodiments of this aspect of the disclosure, the divalent metal can be manganese.

In embodiments of this aspect of the disclosure, the divalent metal can be detectable by imaging when in the central nervous system of an animal or human subject.

In embodiments of this aspect of the disclosure, the nanoparticle core can further comprise a therapeutic agent desired to be delivered to the central nervous system of the animal or human subject, wherein said agent is attached to, or embedded in, the nanoparticle core.

In embodiments of this aspect of the disclosure, the therapeutic agent can be attached to the nanoparticle core.

In embodiments of this aspect of the disclosure, the therapeutic agent can be embedded in the nanoparticle core.

In embodiments of this aspect of the disclosure, the chitosan, the derivative thereof, the polymerized chitosan, or the derivative thereof, can be cross-linked by a cross-linker selected from the group consisting of: L-(+)-Tartaric acid, ethylenediamine-N,N;,N;-triacetic acid, protoporphyrin IX, nitrilotriacetic acid, mercaptosuccinic acid, and ethylenediaminetetraacetic acid.

In embodiments of this aspect of the disclosure, the nanoparticle core can have a biocompatible layer disposed on the surface of said nanoparticle core and the divalent metal can be disposed on, or embedded in, the biocompatible layer, and wherein the divalent metal is available for binding to a cell surface receptor.

In embodiments of this aspect of the disclosure, the biocompatible layer can further comprise a moiety having affinity for the divalent metal.

In embodiments of this aspect of the disclosure, the moiety having affinity for the divalent metal ion can be poly(L-histidine) or a chelating agent.

In embodiments of this aspect of the disclosure, the therapeutic agent to be delivered to the central nervous system of an animal or human subject can be selected from a nucleic acid, a protein, a peptide, a therapeutic agent, or a combination thereof.

In embodiments of this aspect of the disclosure, the nucleic acid can be a single strand DNA, a double-strand DNA, a single strand RNA, or a double-strand DNA.

In embodiments of this aspect of the disclosure, the nucleic acid can be selected from the group consisting of: a polynucleotide, an oligonucleotide, an expression vector comprising a nucleotide sequence desired to be expressed in a recipient cell of the central nervous system of an animal or human subject, an isolated nucleic acid, or a recombinant nucleic acid.

In embodiments of this aspect of the disclosure, the nucleic acid can be an siRNA.

In embodiments of this aspect of the disclosure, the therapeutic agent to be delivered to the central nervous system of an animal or human subject can be selected from a nucleic acid, a protein, a peptide, a therapeutic agent, or a combination thereof, wherein the nucleic acid is a single strand DNA, a double strand DNA, or an RNA, and wherein said nucleic acid is selected from the group consisting of: an oligonucleotide, a vector comprising a nucleotide sequence desired to be expressed in a recipient cell of the central nervous system of an animal or human subject, an isolated nucleic acid, and a recombinant nucleic acid.

In embodiments of this aspect of the disclosure, the nucleic acid is an siRNA.

Yet another aspect of the disclosure encompasses embodiments of a pharmaceutical composition comprising a nanoparticle delivery vehicle according to claim 13 and a pharmaceutically acceptable carrier, wherein said pharmaceutical composition is formulated for administering the nanoparticle delivery vehicle to the nasal epithelium for binding of the delivery vehicle to a divalent metal transporter protein.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Preparation of Chitosan-Manganese Oxide Nanoparticles

Synthesis of manganese oxide nanoparticles: To synthesize manganese oxide nanoparticles, Mn(acac)$_2$ complex, 1,2-dodecanediol, oleic acid, and oleylamine were dissolved in 20 ml of benzyl ether under argon gas protection in flame-dried three neck round bottom flask. The mixture was then heated to 300° C. with vigorous stirring under a flow of argon gas. When the reaction temperature reached 300° C., the initially red color solution became transparent. Around 300° C., the color of the reaction mixture turned to pale green. This color change indicated that the manganese oleate complex was thermally decomposed to generate manganese oxide nanoparticles, whereupon nucleation occurred. The reaction mixture was maintained at this temperature for 1 hr to induce sufficient growth. The solution was then cooled to room temperature, and 100 ml of ethanol was added to precipitate the nanoparticles and separated via centrifugation. The supernatant was discarded and the product was dissolved in hexane in the presence of oleic acid and oleylamine.

Preparation of water soluble manganese oxide nanoparticles: To prepare water soluble manganese oxide nanoparticles, a hexane dispersion of hydrophobic manganese oxide nanoparticles was added to a suspension of tetramethylammonium 11-aminoundecanoate in dichloromethane. The mixture was shaken for 24 hr and the precipitate was separated by centrifuge and washed with dichloromethane. The resulting hydrophilic manganese oxide nanoparticles were dispersed in deionized water (30mg/ml) and stored at 4° C. for further use.

Example 2

Preparation of chitosan-manganese oxide:DNA complex: manganese oxide solution was mixed with 1% water soluble chitosan and then complexed with DNA in PBS solution. The nanoparticles comprising chitosan and a plasmid DNA were made using the protocols as described in Parmaceutical Res. (2007) 24: 1, incorporated herein by reference in its entirety. Preparation of Thiolated Chitosan and Plasmid DNA: Chitosan (MW 33 kDa, degree of deacetylation >90%, viscosity 2.8 cps at 0.5% solution in 0.5% acetic acid at 20° C., Taehoon Bio. Korea) 0.5 g was dissolved in 50 ml of aqueous acetic acid solution (1.0%) to which 400 or 100 ml of thioglycolic acid (TGA) was added. To activate the carboxylic acid moieties of the TGA, 0.5 g of 1-ethyl-3-(3-dimethylaminopropyl) carbodiimide hydrochloride (EDAC) was added. The pH of the solution was adjusted to 5.0 using 1 mM NaOH and the chemical reaction was allowed to run at room temperature for 5 h. To eliminate unbound TGA and isolate the conjugated polymers, the reaction mixture was dialyzed (molecular weight cut-off 6 kDa). The chitosan conjugate was lyophilized at −30° C. and stored at 4° C. until further use. The degree of chemical modification of the chitosan-thioglycolic acid conjugate was determined spectrophotometically by measuring thiol groups at room temperature using Ellman's reagent, 5,5'-dithiobis (2-nitrobenzoic acid) at a wavelength of 412 nm (see Bernkop-Schnurch et al., (2003) *Int. J. Pharm.* 260: 229-237; Roldo et al., (2004) *Eur. J. Pharm. Biopharm.* 57: 115-121, Langoth et al., (2006) *Pharm. Res.* 23: 573-579, incorporated herein in their entireties). A plasmid (pEGFP-N2, 4.7 kbp, Clontech, USA) containing the human cytomegalovirus (CMV) promoter and enhanced green fluorescent protein gene was amplified in *Escherichia coli* and purified using GenElute HP Plasmid Maxprep Kits (Sigma, USA). For cellular uptake studies, the plasmid was labeled with TM-rhodamine (Mirus, Wis.).

Preparation and Characterization of Chitosan/pDNA Nanocomplexes: Chitosan/pDNA nanocomplexes were prepared by mixing chitosan (2 mg/ml) and pDNA (2 mg/ml) solutions in phosphate buffer at pH 6.2. The chitosan/pDNA charge ratio was determined assuming a molecular weight of pDNA of 325 g/mol and one negative charge per DNA base. Positive charge units were calculated assuming one positive charge per amine group adjusted for the degree of deacetylation of chitosan. The loss of amine groups after thiolation was not considered in the calculation of positive charges of thiolated chitosans. Nanocomplexes of thiolated chitosan with pDNA were incubated at 37° C. for 12 h to oxidize thiol groups to crosslink thiolated chitosan in the nanocomplexes. Particle size and zeta potential of chitosan/pDNA nanocomplexes were measured using a Nicomp380/ZLS (Particle Sizing Systems Inc., USA) at 25° C.

Example 3

Synthesis of chitosan nanoparticles based on reverse microemulsion system: Cross-linked nanoparticles were obtained by mixing separately prepared chitosan and cross-linker agent micro-emulsions. First, a chitosan solution was prepared by dissolving 1.0 g of chitosan powder in 100 ml of 0.25% acetic acid. Cyclohexane, n-hexanol and chitosan solution were mixed in a flask in a fixed ratio of 2.75:1:1 (v/v). The chitosan micro-emulsion was formed by adding Triton X-100 drop by drop into the mixture under vigorous stirring until the mixture became transparent. The "water in oil" micro-emulsion of cross-linker was prepared following the same procedure but the diacid was previously activated with N-(3-Dimethylaminopropyl)-N'-ethylcarbodiimide hydrochloride (EDC) and N-hydroxysuccinimide (NHS). To ensure the efficient activation, the cross-linker and NHS were first mixed in water for 15 min and then EDC was gradually added. The ratio between EDC, NHS and carboxyl group was 5:2:1 (v/v) and the pH adjusted to 5.4 by the addition of 2 M NaOH solution. The mixture was stirred at room temperature during 4 h. The crosslinking reaction took place during 24 hr at room temperature after the addition of the cross-linker micro-emulsion into the chitosan micro-emulsion. The nanoparticles were isolated and washed by dispersion in ethanol followed by centrifugation. Finally, the obtained nanopreparation was dispersed in phosphate buffer, as described by Maite Arteche Pujana et al., (2012) *Polymer* 53: 3107-3116, incorporated herein by reference in its entirety.

Example 4

All nanoparticle preparations were tested in vitro cell culture. Human neuroblastoma SH5Y-SY cells were purchased from Sigma-Aldrich and handled according to the supplier protocol. To perform nanoparticle uptake experiments, cells were seeded in 24-well plates (Costar, Ill., USA) and incubated until they formed a confluent monolayer. Upon reaching confluence, the culture medium was replaced by transport buffer (Hank's balanced salt solution, HBSS, pH 7.4) and pre-incubated at 37° C. for 30 min. After equilibration, cell uptake of nanoparticles was initiated by exchanging the transport medium with 500 μL of specified nanoparticle suspension (10 μg/mL to 50 μg/mL in HBSS) and incubating the cells at 37° C. for 24 h. The experiment was terminated by washing the cell monolayer three times with phosphate-buffered saline (PBS, pH 7.4) to eliminate excess particles that were not entrapped by the cells. Cells were photographed with an Olympus fluorescence microscope, as shown in (FIG. 8). Cell-associated nanoparticles were quantified by BD Accury C6 flow cytometer. Uptake was expressed as the percentage of fluorescence-associated with cells. Typical flow cytometry results are shown in FIG. 9.

Detailed experimental conditions and transfection efficiency for the different preparations of nanoparticles is presented in Table 2.

TABLE 2

Transfection efficiencies tested in SH5Y-SY neuroblastoma cells for different preparations of nanoparticles.

| # | Crosslinker | Chitosan | N (nmoL) | P (nmol) | N/P | $MnCl_2$ (nmol) | Transfection Efficiency (%) |
|---|---|---|---|---|---|---|---|
| 1 | TA | LM | 19.44 | 0.8 | 24.30 | 0 | 14.4 |
| 2 | TA | LM | 38.88 | 0.8 | 48.61 | 0 | 18.5 |
| 3 | TA | LM | 58.33 | 0.8 | 72.91 | 0 | 55.6 |
| 4 | PP | LM | 11.66 | 0.8 | 14.58 | 0 | 30 |
| 5 | TA FITC | LM | 5 | 0.8 | 6.25 | 0 | 6.35 |
| 6 | EDTA | LM | 7.5 | 0.8 | 9.37 | 0 | 15.6 |
| 7 | EDTA | LM | 15 | 0.8 | 18.75 | 0 | 39.5 |
| 8 | EDTA | LM | 22.5 | 0.8 | 28.12 | 0 | 46.9 |
| 9 | EDTA | LM | 7.5 | 0.8 | 9.37 | 2 | 21.6 |
| 10 | EDTA | LM | 15 | 0.8 | 18.75 | 2 | 25.6 |
| 11 | EDTA | LM | 22.5 | 0.8 | 28.12 | 2 | 44.8 |
| 12 | PP | HM | 12.5 | 0.8 | 15.62 | 0 | 5.7 |
| 13 | EDTA | HM | 13.88 | 0.8 | 17.36 | 0 | 5.4 |
| 14 | EDTA | HM | 27.77 | 0.8 | 34.72 | 0 | 13.6 |
| 15 | EDTA | HM | 41.66 | 0.8 | 52.08 | 0 | 24.36 |
| 16 | EDTA | HM | 13.88 | 0.8 | 17.36 | 2 | 4.3 |
| 17 | EDTA | HM | 27.77 | 0.8 | 34.72 | 2 | 12.2 |
| 18 | EDTA | HM | 41.66 | 0.8 | 52.08 | 2 | 11.4 |
| 19 | TA | LM1 | 13.89 | 0.8 | 17.36 | 0 | 41.4 |
| 20 | TA | LM1 | 27.78 | 0.8 | 34.72 | 0 | 57.2 |
| 21 | TA | LM1 | 41.67 | 0.8 | 52.08 | 0 | 71.5 |
| 22 | TA | LM1 | 55.56 | 0.8 | 69.44 | 0 | 63.1 |
| 23 | TA | LM1 | 69.44 | 0.8 | 86.81 | 0 | 75.8 |

TABLE 2-continued

Transfection efficiencies tested in SH5Y-SY neuroblastoma cells for different preparations of nanoparticles.

| # | Crosslinker | Chitosan | N (nmoL) | P (nmol) | N/P | MnCl$_2$ (nmol) | Transfection Efficiency (%) |
|---|---|---|---|---|---|---|---|
| 24 | TA | LM1 | 83.33 | 0.8 | 104.17 | 0 | 49.3 |
| 25 | MSA | LM | 22.22 | 0.8 | 27.78 | 0 | 0.1 |
| 26 | MSA | LM | 44.44 | 0.8 | 55.56 | 0 | 9.1 |
| 27 | MSA | LM | 66.67 | 0.8 | 83.33 | 0 | 25.2 |
| 28 | MSA | LM | 88.89 | 0.8 | 111.11 | 0 | 28.5 |
| 29 | MSA | LM | 111.11 | 0.8 | 138.89 | 0 | 32.1 |
| 30 | MSA | LM | 133.33 | 0.8 | 166.67 | 0 | 35.6 |
| 31 | EDTRA | HM | 11.11 | 0.8 | 13.89 | 0 | 9.9 |
| 32 | EDTRA | HM | 22.22 | 0.8 | 27.78 | 0 | 16.3 |
| 33 | EDTRA | HM | 33.33 | 0.8 | 41.67 | 0 | 21.5 |
| 34 | EDTRA | HM | 11.11 | 0.8 | 13.89 | 2 | 11.9 |
| 35 | EDTRA | HM | 22.22 | 0.8 | 27.78 | 2 | 17.3 |
| 36 | EDTRA | HM | 33.33 | 0.8 | 41.67 | 2 | 22.6 |
| 37 | EDTRA | LM | 5.56 | 0.8 | 6.94 | 0 | 1.3 |
| 38 | EDTRA | LM | 11.11 | 0.8 | 13.89 | 0 | 4.4 |
| 39 | EDTRA | LM | 16.67 | 0.8 | 20.83 | 0 | 4.7 |
| 40 | EDTRA | LM | 5.56 | 0.8 | 6.94 | 2 | 2.9 |
| 41 | EDTRA | LM | 11.11 | 0.8 | 13.89 | 2 | 6.4 |
| 42 | EDTRA | LM | 16.67 | 0.8 | 20.83 | 2 | 12.1 |
| 43 | NTAA | LM | 16.67 | 0.8 | 20.83 | 0 | 7.8 |
| 44 | NTAA | LM | 33.33 | 0.8 | 41.67 | 0 | 10.8 |
| 45 | NTAA | LM | 50.00 | 0.8 | 62.50 | 0 | 10.7 |
| 46 | NTAA | LM | 16.67 | 0.8 | 20.83 | 2 | 6.6 |
| 47 | NTAA | LM | 33.33 | 0.8 | 41.67 | 2 | 8.6 |
| 48 | NTAA | LM | 50.00 | 0.8 | 62.50 | 2 | 15.1 |

LM—low molecular chitosan;
HM—high molecular chitosan;
(a) LM1-low molecular chitosan and ultrafiltration of nanoparticles through 0.2 μm filter: The highest transfection of 75.8% in neuroblastoma cells was reached in experiments with nanoparticles fabricated with LM chitosan and TA cross-linker followed by ultrafiltration through 0.2 μm filters. The transfection efficiency depended on the N/P ratio, showing a maximal value at 70 units, as shown in FIG. 10). Without wishing to be bound by any one theory, the low transfection efficiency at small N/P ratios may be due to an insufficient amount of dsRNA delivered. At N/P ratios greater than optimal, the electrostatic forces holding RNA in the nanoparticle may prevent release of RNA.

Replacement of TA on MSA for cross-linking of the same chitosan lowered transfection efficiency as much as two-fold. Preparations 25-30 (Table 2) demonstrated lower efficiency (FIG. 11) compared with nanoparticle preparations 19-24 (Table 2). Also, the highest transfection rate with MSA cross-linker required a higher N/P ratio of about 170.

Example 5

Incorporation of Mn into the nanoparticle: incorporation of Mn into the nanoparticle using the chelating agent EDTA as a cross-linker allowed assessment of the role of Mn in enhancing transfection of dsRNA into neuroblastoma cells. This role largely depended on chitosan quality. For instance, LM chitosan employed in preparations 6-11 (Table 2) made the EDTA cross-linker efficient in transfection as compared with HM chitosan (preparations 13-18, Table 2). As shown in FIG. 9, manganese resulted in an inhibitory effect when HM chitosan was used, but enhanced transfection efficiency for the LM chitosan preparations (FIG. 13). Also, preparation based on LM chitosan and EDTA revealed a trend towards enhancement of transfection as compared with the same preparation without manganese.

No significant effect of manganese on transfection efficiency was found in preparations 31-36 (Table 2) using HM chitosan and EDTRA as cross-linking agent (FIG. 14). However, when LM chitosan was used for the preparation of nanoparticle with EDTRA as the cross-linker (FIG. 15), the incorporation of manganese enhanced transfection compared with the same preparation without manganese. NTAA cross-linker used for LM chitosan showed increased transfection efficiency at N/P rations greater than 60, as shown in FIG. 16.

We claim:
1. A method of delivering a pharmaceutically acceptable agent via an olfactory nerve to the central nervous system (CNS) of an animal or human subject, said method comprising administering to the nasal epithelium of the animal or human subject a pharmaceutically acceptable composition comprising a nanoparticle delivery vehicle, wherein said nanoparticle delivery vehicle comprises a core comprising a plurality of cross-linked chitosan molecules or cross-linked thiolated chitosan molecules; and a plurality of manganese ions bonded to said cross-linked chitosan molecules or thiolated chitosan molecules, wherein the core further comprises a pharmaceutically acceptable agent attached to, or embedded in, the core, whereupon the divalent metal selectively binds to a divalent metal transporter of an olfactory nerve cell, is internalized by said cell, and migrates at least to the olfactory bulb of the CNS of the recipient animal or human subject.

2. The method of claim 1, wherein wherein the cross-linked chitosan molecules or the cross-linked thiolated chitosan molecules are cross-linked by a chelator selected from the group consisting of: L-(+)-Tartaric acid, ethylenediamine-N, N;,N;-triacetic acid, protoporphyrin IX, nitrilotriacetic acid, mercaptosuccinic acid, and ethylenediaminetetraacetic acid, and wherein the manganese ions are chelated by the chelator.

3. The method of claim 1, wherein the pharmaceutically acceptable agent is a plurality of nucleic acid molecules bonded to the plurality of cross-linked chitosan molecules or cross-linked thiolated chitosan molecules of the nanoparticle core.

4. The method of claim 3, wherein the nucleic acid is an siRNA.

5. The method of claim 1, further comprising the step of detecting the nanoparticle delivery vehicle in the recipient animal or human subject, thereby forming an image of the distribution of the nanoparticle delivery vehicle in a tissue of the central nervous system of an animal or human subject.

* * * * *